US011189369B2

(12) United States Patent
Schulze et al.

(10) Patent No.: US 11,189,369 B2
(45) Date of Patent: Nov. 30, 2021

(54) CHARACTERIZING STATES OF SUBJECT

(71) Applicant: Lifetrack Medical Systems Private Ltd., Singapore (SG)

(72) Inventors: Eric Schulze, Taguig (PH); Brendan Philip Rees, Quezon (PH); Dennis Mejia, Calamba (PH)

(73) Assignee: LIFETRACK MEDICAL SYSTEMS PRIVATE LTD., Singapore (SG)

( * ) Notice: Subject to any disclaimer, the term of this patent is extended or adjusted under 35 U.S.C. 154(b) by 154 days.

(21) Appl. No.: 14/757,721

(22) Filed: Dec. 23, 2015

(65) Prior Publication Data
US 2016/0124581 A1    May 5, 2016

Related U.S. Application Data

(63) Continuation of application No. 14/279,782, filed on May 16, 2014, now Pat. No. 9,223,482, which is a
(Continued)

(51) Int. Cl.
*G06F 3/0486* (2013.01)
*G16H 15/00* (2018.01)
(Continued)

(52) U.S. Cl.
CPC .......... *G16H 15/00* (2018.01); *A61B 5/0022* (2013.01); *A61B 5/0035* (2013.01);
(Continued)

(58) Field of Classification Search
CPC .... G06F 3/0481; G06F 17/212; G06F 3/0486; G06F 17/241; G06F 19/36;
(Continued)

(56) References Cited

U.S. PATENT DOCUMENTS 4,733,354 A    3/1988 Potter et al.
5,751,914 A    5/1998 Coley et al.
(Continued)

FOREIGN PATENT DOCUMENTS

AU    2017201809    4/2017
AU    2015257312    7/2017
(Continued)

OTHER PUBLICATIONS

International Search Report and Written Opinion in corresponding PCT Application No. PCT/IB15/53315 dated Oct. 23, 2015, pp. 1-17.
(Continued)

*Primary Examiner* — Shen Shiau
(74) *Attorney, Agent, or Firm* — Fish & Richardson P.C.

(57) ABSTRACT

Among other things, a user of a browser is exposed simultaneously to three interfaces: A viewing interface for at least one image of a subject that is stored on a device on which the browser is running, a decision support interface that aids the user in determining the state of the subject based on the image, and a template interface that aids the user in capturing uniform descriptive information about the state of the subject. At least two of the viewing interface, the decision support interface, and the template interface operate cooperatively so that actions of the user with respect to one of the two interfaces causes changes in content exposed by the other of the two interfaces.

19 Claims, 20 Drawing Sheets

Related U.S. Application Data continuation of application No. 14/272,021, filed on May 7, 2014.

(51) Int. Cl.

| | | |
|---|---|---|
| *G06F 3/0484* | (2013.01) | |
| *A61B 5/00* | (2006.01) | |
| *G16H 50/20* | (2018.01) | |
| *G06F 40/106* | (2020.01) | |
| *G06F 40/123* | (2020.01) | |
| *G06F 40/134* | (2020.01) | |
| *G06F 40/169* | (2020.01) | |
| *G16H 30/20* | (2018.01) | |
| *G16H 30/40* | (2018.01) | |
| *G06F 3/0481* | (2013.01) | |
| *G06T 7/00* | (2017.01) | |
| *G06T 11/60* | (2006.01) | |
| *A61B 5/055* | (2006.01) | |

(52) U.S. Cl.
CPC .......... *A61B 5/7246* (2013.01); *A61B 5/7282* (2013.01); *A61B 5/742* (2013.01); *A61B 5/748* (2013.01); *A61B 5/7425* (2013.01); *A61B 5/7475* (2013.01); *G06F 3/0481* (2013.01); *G06F 3/0484* (2013.01); *G06F 3/0486* (2013.01); *G06F 40/106* (2020.01); *G06F 40/123* (2020.01); *G06F 40/134* (2020.01); *G06F 40/169* (2020.01); *G06T 7/0014* (2013.01); *G06T 11/60* (2013.01); *G16H 30/20* (2018.01); *G16H 30/40* (2018.01); *G16H 50/20* (2018.01); *A61B 5/0002* (2013.01); *A61B 5/0013* (2013.01); *A61B 5/055* (2013.01); *A61B 5/7264* (2013.01); *A61B 5/743* (2013.01); *A61B 5/7435* (2013.01); *A61B 5/7485* (2013.01); *A61B 2560/0475* (2013.01); *A61B 2576/02* (2013.01)

(58) Field of Classification Search
CPC .... G06F 17/2235; G06F 19/30; G06F 19/321; G06F 19/34; G06F 19/36; G06F 19/3487; G06F 3/0484; G06F 40/169; A61B 5/7425; A61B 5/742; A61B 5/0013; A61B 5/743; A61B 5/055; A61B 5/7435; G16H 50/20; G06T 11/60

See application file for complete search history.

(56) References Cited

U.S. PATENT DOCUMENTS

| | | | |
|---|---|---|---|
| 5,821,933 A | 10/1998 | Keller | |
| 6,021,404 A | 2/2000 | Moukheibir | |
| 6,081,267 A * | 6/2000 | Stockham | G16H 30/20 715/788 |
| 6,277,071 B1 | 8/2001 | Hennessy | |
| 6,424,996 B1 * | 7/2002 | Killcommons | G16H 10/60 709/206 |
| 6,542,579 B1 | 4/2003 | Takasawa | |
| 6,574,629 B1 | 6/2003 | Cooke, Jr. | |
| 6,674,879 B1 | 1/2004 | Weisman | |
| 7,502,445 B2 | 3/2009 | Shi et al. | |
| 7,590,932 B2 | 9/2009 | Britton et al. | |
| 7,606,861 B2 * | 10/2009 | Killcommons | G16H 10/60 709/206 |
| 8,521,561 B2 | 8/2013 | Sasai | |
| 8,560,968 B1 * | 10/2013 | Nair | G16H 40/63 715/839 |
| 9,171,130 B2 | 10/2015 | Gustafson | |
| 9,223,482 B2 * | 12/2015 | Schulze | G06F 3/0486 |
| 10,586,618 B2 * | 3/2020 | Schulze | G06F 40/106 |
| 10,631,825 B2 * | 4/2020 | Lee | A61B 8/463 |
| 10,777,307 B2 * | 9/2020 | Schulze | G06F 3/0484 |
| 2001/0041992 A1 | 11/2001 | Lewis et al. | |
| 2002/0021828 A1 | 2/2002 | Papier | |
| 2002/0111932 A1 | 8/2002 | Roberge | |
| 2002/0131625 A1 | 9/2002 | Vining | |
| 2002/0184325 A1 * | 12/2002 | Killcommons | G06F 16/10 709/206 |
| 2003/0018245 A1 | 1/2003 | Kaufman | |
| 2003/0146942 A1 * | 8/2003 | Helgason | G16H 10/60 705/2 |
| 2004/0059215 A1 | 3/2004 | Nishimura | |
| 2004/0073092 A1 | 4/2004 | Miles | |
| 2004/0107118 A1 | 6/2004 | Harnsberger et al. | |
| 2004/0151358 A1 | 8/2004 | Yanagita | |
| 2004/0197727 A1 | 10/2004 | Sachdeva | |
| 2005/0129176 A1 | 6/2005 | Kokubun et al. | |
| 2005/0165285 A1 | 7/2005 | Iliff | |
| 2005/0192487 A1 * | 9/2005 | Cosentino | A61B 5/0002 600/300 |
| 2005/0226405 A1 * | 10/2005 | Fukatsu | G16H 40/63 380/1 |
| 2005/0228250 A1 * | 10/2005 | Bitter | A61B 5/02007 600/407 |
| 2006/0025670 A1 | 2/2006 | Kim et al. | |
| 2006/0149597 A1 | 7/2006 | Powell et al. | |
| 2006/0242143 A1 | 10/2006 | Esham | |
| 2006/0271403 A1 * | 11/2006 | Iwasa | G06Q 10/10 705/2 |
| 2007/0016853 A1 * | 1/2007 | Abagyan | G06T 19/00 715/251 |
| 2007/0128573 A1 | 6/2007 | Kuo | |
| 2007/0128574 A1 | 6/2007 | Kuo | |
| 2007/0237377 A1 | 10/2007 | Oosawa | |
| 2007/0274585 A1 | 11/2007 | Zhang | |
| 2008/0039692 A1 | 2/2008 | Hirakawa | |
| 2008/0044800 A1 | 2/2008 | Kanada | |
| 2008/0052126 A1 * | 2/2008 | Sasai | G16H 15/00 705/3 |
| 2008/0086335 A1 * | 4/2008 | Matsue | G06Q 10/10 705/2 |
| 2008/0256181 A1 | 10/2008 | Morita | |
| 2008/0312954 A1 | 12/2008 | Ullrich | |
| 2009/0076853 A1 | 3/2009 | Sagawa | |
| 2009/0103790 A1 | 4/2009 | Yamagishi et al. | |
| 2009/0199096 A1 | 8/2009 | Pop-Jordanov et al. | |
| 2009/0245603 A1 | 10/2009 | Koruga et al. | |
| 2009/0248447 A1 * | 10/2009 | Niwa | G06Q 50/24 705/3 |
| 2009/0306514 A1 * | 12/2009 | Imamura | A61B 8/461 600/458 |
| 2009/0327890 A1 * | 12/2009 | Mertz | G16H 10/60 715/716 |
| 2010/0034442 A1 * | 2/2010 | Minakuchi | G16H 15/00 382/128 |
| 2010/0042434 A1 | 2/2010 | Gotthardt et al. | |
| 2010/0188352 A1 * | 7/2010 | Ikeda | G06F 1/1647 345/173 |
| 2011/0028825 A1 * | 2/2011 | Douglas | G06T 7/0012 600/407 |
| 2011/0066635 A1 * | 3/2011 | Moriya | G16H 15/00 707/769 |
| 2011/0075901 A1 | 3/2011 | Nakamura | |
| 2011/0129133 A1 * | 6/2011 | Ramos | G16H 30/40 382/128 |
| 2011/0137132 A1 * | 6/2011 | Gustafson | A61B 5/7264 600/300 |
| 2011/0313258 A1 * | 12/2011 | Chopra | G16H 10/20 600/300 |
| 2012/0015316 A1 | 1/2012 | Sachdeva et al. | |
| 2012/0035963 A1 | 2/2012 | Qian et al. | |
| 2012/0054652 A1 | 3/2012 | Kawagishi et al. | |
| 2012/0130743 A1 | 5/2012 | Gotthardt et al. | |
| 2012/0156664 A1 | 6/2012 | Hurwitz | |
| 2012/0176408 A1 * | 7/2012 | Moriya | A61B 6/465 345/629 |
| 2012/0210204 A1 | 8/2012 | Kramer | |
| 2012/0221347 A1 | 8/2012 | Reiner | |

(56) References Cited

U.S. PATENT DOCUMENTS

| | | |
|---|---|---|
| 2012/0246184 A1 | 9/2012 | Rothschild |
| 2012/0270196 A1 | 10/2012 | Hettrick et al. |
| 2013/0006987 A1* | 1/2013 | Stevenne ............ G06F 11/079 |
| | | 707/737 |
| 2013/0088512 A1 | 4/2013 | Suzuki et al. |
| 2013/0152020 A1* | 6/2013 | Nishiyama .......... A61B 1/0005 |
| | | 715/835 |
| 2013/0326386 A1 | 12/2013 | Vendreil |
| 2014/0049483 A1* | 2/2014 | Kim ..................... G06F 3/0488 |
| | | 345/173 |
| 2014/0149407 A1 | 5/2014 | Qian et al. |
| 2014/0189560 A1* | 7/2014 | Caspi ..................... G16H 40/63 |
| | | 715/771 |
| 2015/0146947 A1 | 5/2015 | Matsumoto |
| 2015/0235008 A1 | 8/2015 | Sasai et al. |
| 2015/0262014 A1 | 9/2015 | Iwamura et al. |
| 2015/0317452 A1 | 11/2015 | Kozuka et al. |
| 2015/0320365 A1* | 11/2015 | Schulze ............... A61B 5/7282 |
| | | 600/408 |
| 2015/0324075 A1* | 11/2015 | Schulze ............... A61B 5/7425 |
| | | 715/760 |
| 2016/0124581 A1* | 5/2016 | Schulze ............... G06F 3/0484 |
| | | 715/209 |
| 2016/0179326 A1* | 6/2016 | Thimmanahalli |
| | | Aswathanarayana ....................... |
| | | G06F 3/0488 |
| | | 715/771 |
| 2016/0210441 A1* | 7/2016 | Schulze ............... G06F 40/134 |
| 2016/0232295 A1* | 8/2016 | Serlie .................... G16H 15/00 |
| 2016/0342738 A1 | 11/2016 | Stalling |
| 2019/0189256 A1* | 6/2019 | Schulze ................. G06T 11/60 |
| 2020/0129155 A1* | 4/2020 | Elgena ................... A61B 8/468 |

FOREIGN PATENT DOCUMENTS

| | | |
|---|---|---|
| EP | 3140722 | 3/2017 |
| WO | WO2004/051516 | 6/2004 |
| WO | WO2007/120904 | 10/2007 |
| WO | WO2012/020429 | 2/2012 |

OTHER PUBLICATIONS

Patent Application from corresponding U.S. Appl. No. 14/272,021, filed May 7, 2014, pp. 1-70.
Patent Application from corresponding U.S. Appl. No. 14/279,782, filed May 16, 2014, pp. 1-65.
Transaction history and pending claims for U.S. Appl. No. 14/272,021 as of Jul. 19, 2018.
Transaction history and pending claims for U.S. Appl. No. 14/979,921 as of Jul. 19, 2018.
Extended European Search Report from European application 15789385.0 dated Dec. 1, 2017 (8 pages).
EPO Communication Pursuant to Rules 70(2) and 70a(2) EPC from European application 15789385.0 dated Dec. 20, 2017 (1 page).
Response to EPO Communication Pursuant to Rules 70(2) and 70a(2) EPC from European application 15789385.0 filed on Jul. 2, 2018 (17 pages).
Response to Philippine office action for corresponding application No. 1-2016-500084 filed on Jul. 13, 2016 (82 pages).
EPO Communication Pursuant to Rules 161(2) and 162 EPC from European application 15789385.0 dated Dec. 14, 2016 (2 pages).
Response to EPO Communication Pursuant to Rules 161(2) and 162 EPC from European application 15789385.0 filed on May 29, 2017 (10 pages).
Australian Examination Report from Australian Application No. 2017201809, dated Nov. 28, 2017, 5 pages.
Australian Examination Report from Australian Application No. 2018206741, dated May 29, 2019, 12 pages.
Australian Office Action from Australian Application No. 2015257312 dated Mar. 10, 2017, 5 pages.
Philippine Office Action for Corresponding Application No. 1/2016/500084, dated Jun. 2, 2016.
EPO Communication Pursuant to Rules 161(2) and 162 EPC from European Application No. 15789385.0, filed on Dec. 14, 2016, 2 pages.
Transaction history and pending claims of U.S. Appl. No. 14/272,021.
Transaction history and pending claims of U.S. Appl. No. 14/279,782.
Transaction history and pending claims of U.S. Appl. No. 14/757,721.
Transaction history and pending claims of U.S. Appl. No. 14/979,921.
Transaction history for Corresponding U.S. Appl. No. 14/279,782, filed May 16, 2014.
Transaction history for Corresponding U.S. Appl. No. 14/757,721, filed Dec. 23, 2015.
Transaction history for Corresponding U.S. Appl. No. 14/979,921, filed Dec. 28, 2015.
PCT International Preliminary Report on Patentability in International Application No. PCT/IB2015/053315, dated Nov. 6, 2016, 14 pages.
Singapore Examination Report in Singaporean Application No. 11201609265R, dated Jun. 26, 2018, 8 pages.
Australian Examination Report No. 2 for Application No. 2018206741, dated Nov. 29, 2019, 3 pages.
Windows.com [online], "Turn drag drop into cut instead of copy", published in 2009, retrieved on Jun. 7, 2021, retrieved from URL<https://www.windows.com>, 5 pages.
Youtube.com [online], "Drag and Drop to Open Files", published on Jul. 28, 2010, retrieved on Jun. 7, 2021, retrieved from URL<https://www.youtube.com/watch?v=bct2ct4syzy&t=132s>, 5 pages.

* cited by examiner

FIG. 3

| # | Patient Name | Patient ID | Accession No | Institution Name | Modality | Body Part | #SE / # | Study Date | Received Date | Description | QA Status |
|---|---|---|---|---|---|---|---|---|---|---|---|
| | ANONYMOUS | 52ecb4b2683bc | 52ecb4b268334 | ANONYMOUS | CR | CHEST | 1/1 | | | CHEST PA | New |
| | ANONYMOUS | 52ecb5a22ee2d | 52ecb5a22eda8 | ANONYMOUS | CR | SKULL | 3/3 | | | MASTOID-TOWNES/LAT/LAWS | Verified |
| | ANONYMOUS | 52ecb6d8bb64c | 52ecb6d8bb54c | ANONYMOUS | MR | HEAD | 4/81 | | | MRI-HEAD | New |
| # | Patient Name | Patient ID | Accession No | Institution Name | Modality | Body Part | #SE / # | Study Date | Received Date | Description | QA Status |

Record: 1-3 of 3  << First  < Previous  Next >  Last >>

Viewer  Search: _____  Hide QA Status  Filter QA Reports

User: _____
Role: LMS Administrator ▼
Institution: Anonymous ▼
User Management  Logout

FIG. 3A institution name
is | is not | does not | begins with | ends with | contains
[____]
Apply  delete  close

Active Templates — 500

Active Template: (DX_CHT_HWY_001.txt)
[REPORT] [RELOAD] [PICK DIFFERENT TEMPLATE]

DX_CHT_HWY_001: 505 — Technique — [PA view] [PA»] [AP»] [and»] [lateral] [and»] [apicolordotic»] [view] [right side down »] [and »] [left side down »] [decubitus views also performed] [a right »] [and»] [a left »] [shallow»] [steep »] [oblique view was also performed] [portions of the »] [right »] [and»] [left »] [costophrenic angles»] [lateral chest »] [and»] [lateral lung »] [is not included on this exam and cannot be evaluated]  ./ 540
532, 536, 534, 538, 548, 542

506 — Comparison [none] [comparison is with study dated] ./ 540, 542

508 — Clinical History [preemployment Physical] [PRE EMPLOYMENT] [Annual Physical Exam] [ape] [APE] [checkup] [R/O PTB] [no»] [cough] [no»] [fever] ./ 540

510 — Impression [clear normal chest] [normal chest] [limited exam as noted] [otherwise unremarkable chest] [clear lungs] [clear visualized lungs] [no acute disease] [clear apicolordotic view] [no acute disease is seen in the visualized lung apices] [while this»] [while these»] [lung nodules may reflect sequela of prior granulomatous infection neoplasm is not excluded] [consider followup with CT] [these finding(s) may reflect] [« prior granulomatous infection] [« chronic granulomatous infection] [« prior TB exposure] [« active granulomatous infection] [« chronic active TB] [« pulmonary tuberculosis of indeterminate activity] ...

⊞ Patient Position [mild»] [moderate »] [severe »] [rightward »] [leftward »] [patient rotation is seen] 513 — [significant patient breathing motion artifact is seen] ... — 512
544
Mediastinum: — 514
516 — Superior Mediastinum [normal] [less...] [normal] [mildly»] [moderately»] [severely »]
546
519 — [widened superior mediastinum] ...
518 — ⊞ Mediastinum [more...] 546
544 — 548
520 — Heart [normal] [more...] ... 546

Cheat sheet                                540

Impression: [clear normal chest] [normal chest] [limited exam as noted] [otherwise unremarkable chest] [unremarkable cardiopulmonary findings] [clear lungs] [clear visualized lungs]
[no acute disease] [clear apicolordotic view] [no acute disease is seen in the visualized lung apices] [while this »] [while these »]
[lung nodules may reflect sequela of prior granulomatous infection] [neoplasm is not excluded] [consider followup with CT] [these finding(s) may reflect »] [« prior granulomatous infection]
[« chronic granulomatous infection] [« prior TB exposure] [« active granulomatous infection] [« chronic active TB] [« pulmonary tuberculosis of indeterminate activity]
⊞ Patient Position: [mild »] [moderate »] [severe »] [rightward »] [leftward »] [patient rotation is seen] [significant patient breathing motion artifact is seen]
Mediastinum:
Superior Mediastinum: [normal] More » ～572
⊞ Mediastinum: More »
Heart: ⊂⊃ [normal] More »
Aorta: [normal] More »
Pulmonary Arteries: ⊂⊃ [normal] More »
⊞ Hilum: More »
Lungs:
Expansion: More »
Diaphragms: [unremarkable] More »
Right Lung: [clear] More »
⊞ Lung Parenchyma: [clear] More »
⊞ Lung Nodule: [none] More »
Left Lung: [clear] More »

Comparison: None.
Clinical History: Annual Physical Exam.
Mediastinum:
    Superior Mediastinum: Normal.
    Heart: Normal.
    Aorta: Normal.
    Pulmonary Arteries: Normal.
Lungs:
    Right Lung: Clear.
    Left Lung: Clear.
Pleura:
    Effusion: None.
Bony Structures:
    Spine: Mild levoconvex scoliosis of the upper thoraciospine.
    Left ribs: Normal.
    Right ribs: Normal.
Impressions:
    1. Mild levoconvex scoliosis of the upper thoraciospine.
    2. Otherwise unremarkable chest. Clear lungs.

[Save] Promote to: [Final] Demote to: [Dictated]  [Cancel Report]
+ Study Thumbnails

FIG. 8A (Cont.)

| Accession Number | 52ecb5a22eda8 |
|---|---|
| Patient ID | 52ecb5a22ee2d |
| Patient Name | ANONYMOUS |
| Birthdate | |
| Sex | Female |

| Modality | CR |
|---|---|
| Body Part | SKULL |
| Study Description | MASTOID - TOWNES/LAT/LAWS |
| Study Date | |
| Reason for Study | HX, INFECTED AND PAIN (R) SIDE |
| Diagnosis Description | |
| Patient Comments | |
| Comparison Study ID's | |

[Active Template V1]  [Active Template V2]

Current Status: Verified          Institution: ANONYMOUS
Last Updated:

There are no comparisons for this study.

Communication Box

Findings

[Show report text]  [Choose another template]  [Reset template]
[Reload template from server]  [Edit Template]  [New Template]

Technique: ⌧ «AP» «and» «lateral» «and» «Waters» «and» «base of skull» «and Towne's» view was performed of the «skull» «and» «paranasal sinuses «mildly» «moderately» undeveloped paranasal sinuses are evident « consistent with patient age «mild» moderate » «severe» «rightward» «leftward» rotation is evident on the PA view «which decreases sensitivity «and« specificity « of the study « mild » «moderate » severe » «rotation » «and» «motion » «and» «underpenetration » «and» «overpenetration»

CHARACTERIZING STATES OF SUBJECT

RELATED APPLICATIONS

This application is a continuation and claims priority to U.S. application Ser. No. 14/279,782, filed May 16, 2014, which is a continuation and claims priority to U.S. application Ser. No. 14/272,021, filed May 7, 2014, the entire contents of which application is hereby incorporated by reference.

BACKGROUND

This description relates to characterizing states of subjects.

In diagnosing a medical condition of a patient, for example, a doctor can apply her experience and knowledge to health-related information about the patient (for example, age, weight, body temperature, symptoms, medical history) to classify the medical condition. Frequently, the health-related information includes images captured by a variety of modalities (x-ray, computed tomography, magnetic resonance imaging). Correlations exist between health related information about populations of patients and medical conditions of those patients that enable an experienced doctor to make an accurate diagnosis. It is commonplace for the doctor then to create a medical report that captures the health-related information and the diagnosis.

Traditionally medical reports are created by hand on paper and stored in paper files associated with the patients. The language used on medical reports to describe medical conditions has become standardized in many cases, and skilled doctors are accustomed to making careful use of the standardized language so that other people who read the reports will find them clear and understandable.

Computer-based systems have been developed to aid medical professionals in accumulating, storing, and analyzing health-related information about patients and in producing clear and accurate medical reports quickly and easily. Among other things, there are templates available that help the doctor to consistently use well accepted terminology and to produce medical reports that are complete and accessible quickly to others.

The quality and accuracy of the classification and characterization of states of subjects varies widely depending on the skill, experience, education, training, and other factors associated with the people doing the classification and characterization. For example, in some areas of the world, pathologists perform their work less effectively, less efficiently, and less accurately than in other areas of the world, due largely to less adequate or suboptimal educational opportunities, among other things.

SUMMARY

In general, in an aspect, a user of a browser is exposed simultaneously to three interfaces: A viewing interface for at least one image of a subject that is stored on a device on which the browser is running, a decision support interface that aids a determination of the user about a state of the subject based on the image, and a template interface that aids the user to capture uniform descriptive information about the state of the subject. At least two of the viewing interface, the decision support interface, and the template interface operate cooperatively so that actions of the user with respect to one of the two interfaces causes changes in content exposed by the other of the two interfaces.

Implementations may include one or a combination of any two or more of the following features.

The template interface includes interactive controls that represent templated structured content; interaction with the interactive controls is reflected in a digitally stored record associated with the subject. The subject includes a person, and the state includes a medical state of the person. The browser includes Google Chrome. The interfaces are device independent and operating system independent. The subject includes a person, and the uniform descriptive information includes part of a medical report. The subject includes a person, and the images include images generated by at least one medical imaging modality. The images are downloaded by the browser and stored on local storage. The images are DICOM compliant. The images stored on the device have been received from a server. The template interface has at least one interactive user feature, and the tool of the viewing interface is sensitive to the feature.

The viewing interface includes at least one tool that aids the user in interacting with the images. The tool is context-sensitive. The context to which the tool is sensitive includes an imaging modality or a part of the subject that is imaged or both. The template interface provides interactive controls that represent selections, or choices, or modifiers, and interaction with the controls governs at least a part of the descriptive information that is captured about the state of the subject. The viewing interface includes at least one tool that aids the user in understanding the images, and the tool is contextually sensitive to user interaction with the interactive controls of the template interface. The viewing interface includes tools that aid the user in understanding the images, and the tools are contextually sensitive to user interaction with the interactive user controls of the decision-support interface. The tool has a feature that is sensitive to at least one context of at least one of the interfaces exposed to the user. At least one image is associated with a part of the subject, and the feature of the tool is sensitive to the part of the subject. At least one image was captured using a particular modality, and the feature of the tool is sensitive to the modality.

The decision-support interface displays at least one of a diagram, an image, or a text element associated with states of subjects, and includes interactive user controls. The decision support interface has at least one interactive user feature, and the tool of the viewing interface is sensitive to the feature.

The tool represents at least one normal value that is sensitive to an attribute of an image to which the tool may be applied. The tool has a feature that aids the user in using the tool. The feature includes a visible indicator on the viewing interface. The feature is provided in the decision support interface. The feature in the decision support interface includes at least one normal or abnormal example or diagram. A use of the tool causes at least one value associated with the tool to be associated with a feature of the template interface. The use of the tool includes a dragging and dropping of the tool or an image to which the tool has been applied in the viewing interface, into the template interface of the decision support interface. The use of the tool includes a context sensitive application of the tool to the image.

At least one of the images is associated with stored attributes, and use of a feature of the template interface causes an annotation of the stored attributes of the image. At least one of the images is associated with stored attributes, and use of a feature of the decision support interface causes an annotation of the stored attributes of the image. At least two of the interfaces are associated with stored attributes associated with images, templates, or decision support elements, and at least some of the attributes are expressed as objects that include values and methods. Values of at least some of the attributes are changed in response to actions by the user in using at least one of the interfaces.

In general, in an aspect, information is stored about images of a subject, content of a report is stored that includes uniform descriptive information about a state of the subject, and elements of a decision support system are stored that are useful in determining the state of the subject. The information is stored as programming objects that contain values of attributes and methods associated with the attributes. The value of at least one of the attributes of one of the objects can be changed by executing a method of one of the objects based on interaction of a user with one of the images, with a template for the report, or with an element of the decision support system.

In general, in an aspect, a user is exposed, through an interface of a browser, to a facility for use in determining a state of a subject, based on (a) information presented to the user about attributes of the subject and (b) information about relationships between states of other subjects and attributes of the other subjects. The facility interactively guides the user in determining the state of the subject by presenting interactive controls representing possible attributes of the state of the subject to the user. The interactive controls and the facility respond (1) to interaction by the user with the controls and (2) automatically to information about relationships between states of other subjects and attributes of other subjects provided from the app or through the browser. The interaction by the user with the controls includes touching a display. The facility exposed to the user through the interface enables the user to generate a report determining the state.

Implementations may include one or a combination of any two or more of the following features. Determining the state of the subject includes classifying the state of the subject by classifying information associated with the subject based on normative aggregated information associated with other subjects. Classifying the state of the subject includes diagnosing a medical state of a person. The information presented to the user includes images associated with the subject. The interactive controls include text phrases that can be part of a text report of the state of the subject. The interaction by the user with the controls includes the user indicating features of the state of the subject based on the information presented to the user about the attributes of the subject. The relationships between the states of other subjects and attributes of the other subjects are based on expert knowledge. The relationships between the states of other subjects and attributes of the other subjects are part of a decision support system.

Information is presented to the user through the interface about the relationships between the states of other subjects and attributes of other subjects using diagrams and examples, e.g., of prior subjects. The interactive controls representing possible attributes are presented in a stepwise manner representing expert knowledge. Expert knowledge is embedded in the information about relationships between states of other subjects and attributes of the other subjects, and the expert knowledge is made available to the user based on a context implied by Interactions of the user with the facility used in determining the state of the subject.

The interactive controls representing possible attributes are presented in at least two different modes suitable respectively for users of different skill levels. The interactive controls representing possible attributes are presented in a collapsed mode for a user who can determine the state of the subject without requiring presentation of decision support information. The collapsed mode enables the user to generate a report of the state of the subject by noting only what is abnormal or requires a comment. The interaction by the user with the controls includes dragging and dropping images that represent attributes of the subject onto text associated with the controls. The images are automatically annotated with attributes based on the text onto which the images are dropped. Dropping of an image onto text associated with the controls causes the text associated with at least one of the controls to expand to include additional uniform text representative of knowledge provided by a subject matter expert. The interactive controls are associated with attributes of the subject and the interactive controls include links to decision support elements associated with the attributes.

The decision support elements include diagrams or examples. A user can invoke one or more of the decision support elements and, in response to an invocation of one of the decision support elements, corresponding interactive controls of the state determining facility are updated automatically. Decision support elements are automatically appended to a report generated by the state determining facility.

A second user can interact with the interactive controls of the state determining facility to change interactions of the first user, and differences between the two interactions can be measured as an evaluation of the skill of one of the users. The attributes of interactive controls of the facility as set by the user and as set by other users are exposed to the user as feedback. The other users include people who have determined with certainty from the subject the accuracy of the determination of the state of the subject. The user can identify through the interface, information about the subject as representing an example of a determination of states of similar subjects represented by elements of a decision support system, and automatically updating the decision support system to include the example.

In general, in an aspect, a user is exposed through an interface of a browser to a decision support facility that uses decision support information to aid the user in expressing a state of a subject based on attributes of the subject. The user interface provides viewing features that enable a user to identify attributes of the subject for use by the decision support facility. The user interface provides a determination facility enabling the user to express the state of the subject through interactive controls. The decision support facility uses the user's expressions of the state of the subject to provide decision support information.

Implementations may include one or a combination of any two or more of the following features. The decision support facility follows the user's expressions of the state of the subject step by step and presents relevant decision support information for each step in turn. The decision support facility follows the user's invocation of respective interactive controls and presents relevant decision support information for each of the controls. The decision support information that is provided causes automatic updating of the interactive controls. The determination facility reflects information provided by a subject matter expert based on user's expressions of the states of subjects. The decision support information that is provided includes examples of normal, abnormal, and normal variants. The decision support information that is provided includes indications of tools to use to capture attributes of the subject. A database of examples used by the decision support facility is automatically updated to include examples identified by the user in using the state determination facility.

A user may drag and drop an image from the viewing interface onto the template interface, from the viewing interface onto the decision support interface, or from the decision support interface onto the template interface, or any combination or two or more of those. When an image is dragged and dropped, a review is triggered to be done by a person who has experience in understanding a relationship between the image and the state of the subject. If information entered into the template interface by the user is indicative of a critical finding that requires time sensitive action, an automatic notification is sent to a party for action. The template interface aiding the user includes displaying, in response to the user interaction with elements of the template interface, information that guides the user in selecting elements of the template interface for inclusion in a report about the state of the subject. The information that guides the user is determined by a subject matter expert.

Data is provided to a radiology information system (RIS) indicative of times associated with an image. The times include at least one of a time when the image is sent, a time when an analysis of the image is done, and a turnaround time. An excellence score is derived for the determination of the user about the state of the subject based on the image. The excellence score is based on elapsed time, efficiency, and quality. The excellence score is based on a severity or conspicuity level of the state of the subject.

A report generated by the template interface is communicated to a party other than the user who has knowledge of an actual state of the subject. The party can report information related to the actual state of the subject, and the information reported by the party is stored for use in correlating the determination of the state of the subject made by the user and the information related to the actual state of the subject. The times and sequence of steps of user interaction with the interfaces are recorded for later playback.

An analysis is done of the determination about the state of the subject, structured data associated with the image, and information that correlates states of subjects with the structured data, as a check of the likely appropriateness of the determination about the state of the subject. The structured data includes an age of the subject, and the information correlates a pathology with an age range. The structured data includes a DICOM header. The check is made at the time a user is making a proposed determination. Data is stored in a radiology information system (RIS) that associates efficiency related timestamps with images for which corresponding users of the template interface have captured uniform descriptive information about the state of the subjects. Scores are assigned to users of the template interface based on efficiency related timestamps of images.

Elements presented by the template interface are altered to indicate to a particular user an aspect of the uniform descriptive information that requires attention by that user. The altering of the elements is based on past performance of the user with respect to similar images. The altering of the elements includes requiring the particular user to choose positively or negatively whether an element of the uniform descriptive information is present or absent. The altering of the elements includes changing the color of the elements. The user is provided real-time feedback in the template interface based on information about the user, the subject, or the uniform descriptive information. The real-time feedback includes notifications about errors made by the user. The real-time feedback includes other states of the subject commonly associated with the current state of the subject being described. For example, the real-time feedback includes notifications associated with syndromes or common co-morbidities suggested by the user's capturing of certain uniform descriptive information about the state of the subject. Uniform descriptive information associated with a right side or a left side of the subject is made available to the user. The decision-support interface displays predetermined pathologic presentations and descriptions of the pathologic digital presentations in words commonly used by a subject matter expert (SME). The commonly used words depend on a stage of a developing state of the subject. The user can invoke the commonly used words of the subject matter expert displayed in the decision-support interface and causing the commonly used words to appear in the template interface.

These, and other features, aspects, and implementations, and combinations of them can be expressed as methods, methods for doing business, software products, systems, components, apparatus, methods, and in other ways.

Other features, objects, and advantages will be apparent from the description and drawings, and from the claims.

DESCRIPTION

FIG. 3 shows an example of a worklist.

FIG. 3A shows an example of a pop up in a worklist.

FIG. 5 shows an example of an active template.

FIG. 5B shows an example of an active template in a guided mode.

FIG. 8B shows an example of an active template while the report is in a verified status.

Figure 1:
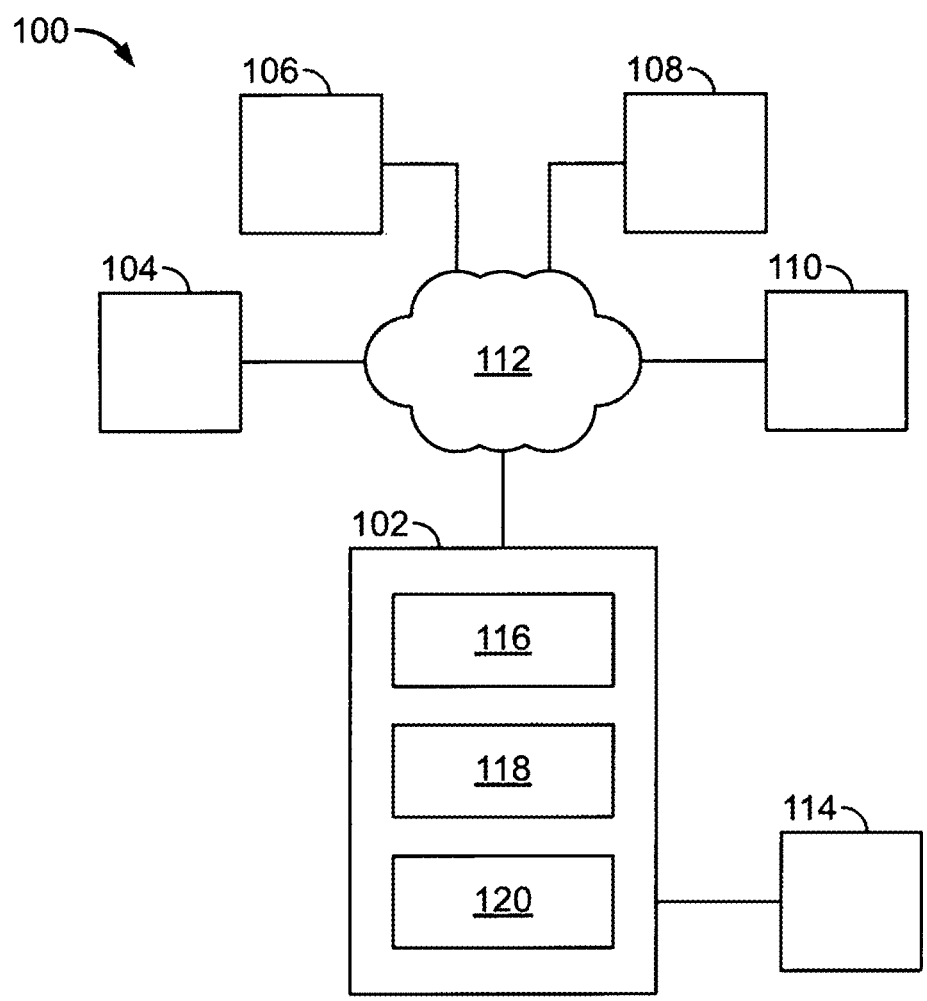
FIG. 1 is a block diagram of a system for use in classifying structured contents.

Among other things, we describe here systems and techniques that provide, in an integrated and seamless way, features and facilities to: (1) enable subject matter experts in a field to capture, store, correct, and update their knowledge and experience about correlations between information (e.g., structured content) that is indicative of the state of a population of subjects and the actual states of those subjects; (2) enable users to characterize (e.g., classify) the actual or believed states of other subjects based on information (e.g. structured content) that is indicative of the states of the other subjects; (3) provide user interfaces that govern interactivity between users and the user interfaces in a way that implicitly represents the stored knowledge and experience of the subject matter experts, and guides and enables the users to achieve clear and accurate characterizations and classifications (that conform to standard ways of expressing the characterizations and classifications) of the states of the subjects; (4) use characterizations produced by users with respect to states of subjects to improve stored information about the correlations, the characterizations, and classifications; (5) provide interaction and feedback between users of the featured facilities, including users of different levels of experience and skill; (6) evaluate users based on the quality, speed, effectiveness, clarity, and completeness of their characterizations and classifications; (7) educate and train the users; (8) provide a hardware and operating system independent, efficient, rapid, and easy to use way to view high-quality images anywhere in the world and seamlessly link the user's activities with respect to the images with the user's activities in characterizing and classifying the conditions of the subjects, and in studying information provided by decision-support systems; and (9) enable users to translate the information and characterizations and classifications of the information produced by the users and the systems and techniques into a different language, so that the systems and techniques can be readily available in another language.

In the course of our description, we sometimes use each of the following terms broadly to include, for example, the categories and instances referred to below:

Viewer or viewer interface—a feature that presents visual data, such as images, for viewing by a user, for example, a user who is viewing and working with the images in connection with classifying the condition of the subject. In some examples, the viewer or viewer interface can be engineered to present DICOM compliant image data along with context sensitive user tools that allow for manipulation of the image for visualization of image findings, or to make measurements of size or other characteristics related to the images (angles, attenuation, volume, etc.) or for other purposes. In some cases, the viewer can be an actual subject, instead of visual data for the actual subject. For example, when an internist performs a structured physical exam on an actual patient, the patient becomes the viewer. The internist can work with the viewer, along with other systems, e.g., a template or active template for History and Physical, and a decision support system, both of which are described below.

Decision support system—a system that supports a user in making decisions that characterize her classification of the conditions of subjects. In some examples, the system can include a knowledge base that contains both static knowledge related to the subject (such as anatomy, normal and abnormal findings, normal ranges related to measurements, age of subject, position of finding within an anatomic structure) as well as dynamic data based on images (anonymized) which represent examples of normal and abnormal findings. In some cases, the decision-support system comprises a large number of stored elements or objects that represent the static knowledge and dynamic data. The elements or objects can be tagged with essentially unlimited attributes which relate to their context sensitive presentation to the user as well as their behavior when dragged into a report or clicked to produce changes in either active templates or the viewer interface.

Template or active template—a set of one or more canonical sentences each of which contains one or more possible words or phrases in a sequence such that any two or more of the words or phrases within the ordered sequence can potentially form a sentence—that is descriptive of a condition of a subject. Taken together, the set of canonical sentences represent statements that characterize or classify the vast majority (or all) of the findings about the condition of the subject. For example, the set of canonical sentences together might represent essentially all the possible findings about the condition of the subject that is represented by a specific radiographic study, such as a study done using a particular modality evaluating a particular body part (e.g., X-ray Chest, or CT abdomen). In some cases, the template or active template essentially represents a routine checklist that would be used by a trained person, such as a radiologist. Use of subject matter experts to build templates allows the templates to incorporate best practices in use of terminology, order of report findings, and appropriate descriptors. It also allows the effortless use of even complex tools which are prompted by making a simple finding. (For example, findings may be easy to see on an image, but remembering which angle tool to use to quantify the severity may be difficult for a generalist). The net effect is to make even a generalist capable of rendering an expert level report. A template can be active, for example, if a user interaction with the template (or other information from a decision-support system or from a viewer) causes the template to change its form or content or both.

Interface—a presentation (for example, visual) of information, for example, on a computer screen, which the user interacts with to perform functions related to their role in the system. For example, an interface could have three features or be comprised of three interfaces, such as a viewer, and active template, and a decision-support system. Among other things, in some examples, interfaces allow the user to view unique information and classify the information into structured reports through the use of integrated active templates and decision-support systems. Two or three interfaces can be presented simultaneously on one or more computer screens. For example, a left screen of two screens arranged side by side can show the decision support system and an active template and a right screen can show a viewer.

Image—any kind of visual or graphical information that the user uses in classifying or characterizing a condition of the subject. In radiology, for example, the image can be a diagnostic image, such as photographic films, ultrasound, CAT scan, MRI, nuclear medicine scan, and mammograms. In some implementations, these images are what are presented in the browser based viewer. In some implementations, the image is the visual information of an actual subject, e.g., an actual patient.

Tool—includes any device used within the viewer to manipulate the images or measure or test characteristics of the images. In some implementations, the manipulation tools include but are not limited to: magnification, pan, window level, rotate, flip, scroll (through a stack of images—such as in CT or MRI). Also included in some cases are tools for measurements such as linear distance/size, volume, Hounsfield units (measurement of x-ray attenuation—roughly electron density of matter), angle(s), and any number of context sensitive measurement tools auto chosen through the use of the decision-support system and active templates. Examples include the spine disc bulge measurement tool for spine MRI studies, and Boehler's angle of the calcaneus in a calcaneus fracture. In some implementations, for a structured physical exam, the tools can also include a blood pressure cuff. In some implementations, the tools have wireless connectivity, and the tools can automatically power up when the tools need to be used. For example, the blood pressure cuff can be automatically powered up when the blood pressure portion of the History and Physical needs to be performed.

DICOM—includes the Digital Imaging and Communications in Medicine protocol that provides a standard file format specifying how medical images are stored and presented along with information about the patient and the image such that any DICOM compliant viewer can present a DICOM compliant image. It also defines the communication protocol (over TCP/IP) used to transmit the images Attribute—data or functions associated with objects or records. In some implementations, the attributes can be assigned or triggered through selection (by, for example, either mouse click of or drag and drop of an image or diagram into an element in the active template.

Value—typically a number and its associated unit. In some implementations, when the element is chosen, the attribute value that was encoded in the element is automatically associated with the image with the user and placed in the database as well as on the image as appropriate.

Context sensitive—for example, encoding the use of specific tools based on information known to the integrated system, such as the modality, the body part, the institution, patient demographic data including patient age and sex, the chosen element in an active template, the position within an active template, or the chosen diagram or example image in the decision-support system, or any combination of two or more of those.

Object-oriented programming—a method of programming in which each object (for example, a group of cohesive lines of code) has its functions encapsulated wholly within the code. In some implementations, each element of the active template is encoded as an object which is assigned attributes that are related to the element which will be entered into a database (in the case of a data attribute) or a function such as a viewer tool choice which is displayed simply based on choosing the object.

Objects—in some cases, objects are called elements in both the active templates and the decision-support system; the objects function similarly to an object-oriented programming object in the sense that the attribute is essentially encapsulated within the element that can be chosen.

Guided mode—in some implementations, in this mode, the active template, for example, is presented essentially line by line to the user. In some cases, a beginner user (usually a person without much experience) is asked to evaluate an image for classification one criteria at a time. For example, the beginner can be asked to evaluate heart size on a chest x-ray, followed by evaluating the aortic configuration. In guided mode, in some cases, the active template presents one structure or finding to be evaluated at a time while the decision-support system similarly presents information relevant to correctly classifying the image related to the criteria being evaluated.

Expert mode—in some cases, in an expert mode, the expert user can view the entire active template at one time.

Feedback—for example, in a dual read mode feedback is an automatic result when there is a discrepancy between a report (classification) of a beginner user and a quality assurance user.

FIG. 1 shows a system 100 for users 105, 107, 109, to view, learn about, analyze, categorize, classify, or make decisions (or any combination of those) regarding structured content that is stored in and retrievable from one or more servers 102 through one or more user systems 104, 106, 108, 110 connected to the server(s) 102 directly or through a network 112. In some implementations, the content and functions of the system are made available to the users by web servers associated with the servers 102 and web browsers running on the user systems. The user systems can be workstations, notebooks, tablets, pads, mobile phones, and other fixed and portable devices. Examples of structured content include medical images, e.g., diagnostic images, that are in compliance with DICOM (Digital Imaging and Communications in Medicine). DICOM is a standard file format specifying how medical images are stored and presented along with information about the patient and the image such that any DICOM compliant viewer can present a DICOM compliant image. DICOM also defines communication protocols, e.g., over TCP (Transmission Control Protocol)/IP (Internet Protocol), for use in transmitting the medical images. Examples of diagnostic images include radiology images, e.g., including DX (Digital Radiography in plain films) images, US (Ultrasound) images, CT (X-ray Computed Tomography) images, MRI (Magnetic Resonance Imaging) images, nuclear medicine scan images, and mammograms. In some implementations, the structured contents are medical charts, e.g., standard History and Physical information, or non-medical related information, e.g., accident investigation information, crime scene investigation information, restaurant menus, and interactive education and testing scenarios. In some implementations, the structured contents are stored in one or more databases 114 that is part of the server(s) 102 or connected to the server(s) 102.

The user systems 104-110 can be computer systems that include displays for displaying information to the users. In some implementations, the computer systems include input devices, e.g., keyboards, for the users to provide input into the user systems. The computer systems may also include a touch screen through which the user inputs information to the computer systems. In some implementations, the user systems 104-110 are handheld devices or mobile devices, e.g., a pad, tablet, or a smart phone. The network 112 can be Internet or other networks, e.g., LAN (local area network), VPN (virtual private network), or WAN (wide area network). Example users of the system 100 include individuals, such as medical professionals of different roles including doctors, nurses, and others, or system administrators, and entities, such as hospitals.

The server(s) 102 can store and support one or more viewers 116, one or more active templates 118, and d one or more decision support systems 120, each of which can be displayed to a user through an interface to allow the user to act on the structured contents stored in the database(s) 114. In some implementations, the viewer(s) 116, the decision support system(s) 120 and the active template(s) 118 reside on the same domain, which is the recognizable name associated with an IP address for an internet resource, e.g., a server on the public internet, so that they may interact with each other with a unique level of integration. At least part of the viewer(s), the template(s), and the decision support system(s) is embodied in computer programs.

An interface can be understood as visual presentation of information on a screen with which a user interacts to perform functions related to his/her role. In the example of the system 100, the interfaces for the viewer(s), the active template(s), and the decision support system(s) are integrated such that, change of the content in one interface can be automatically populated into the other interfaces such that the contents of the other interfaces are consistently updated. The interfaces can allow a user to view and classify structured contents into structured reports.

Figure 2:
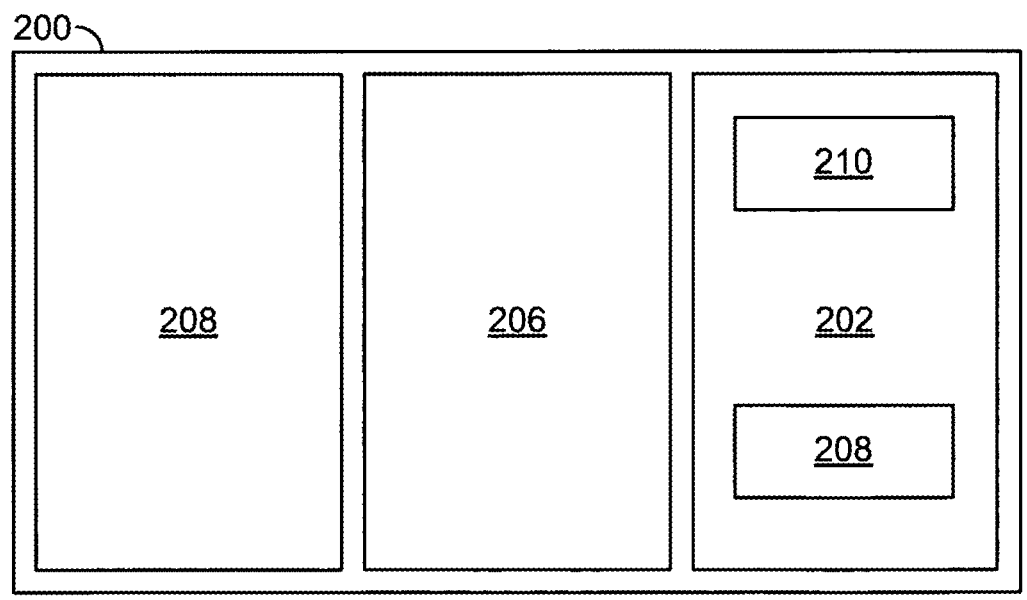
FIG. 2 is a block diagram of a screen simultaneously displaying three interfaces.
Figure 2A:
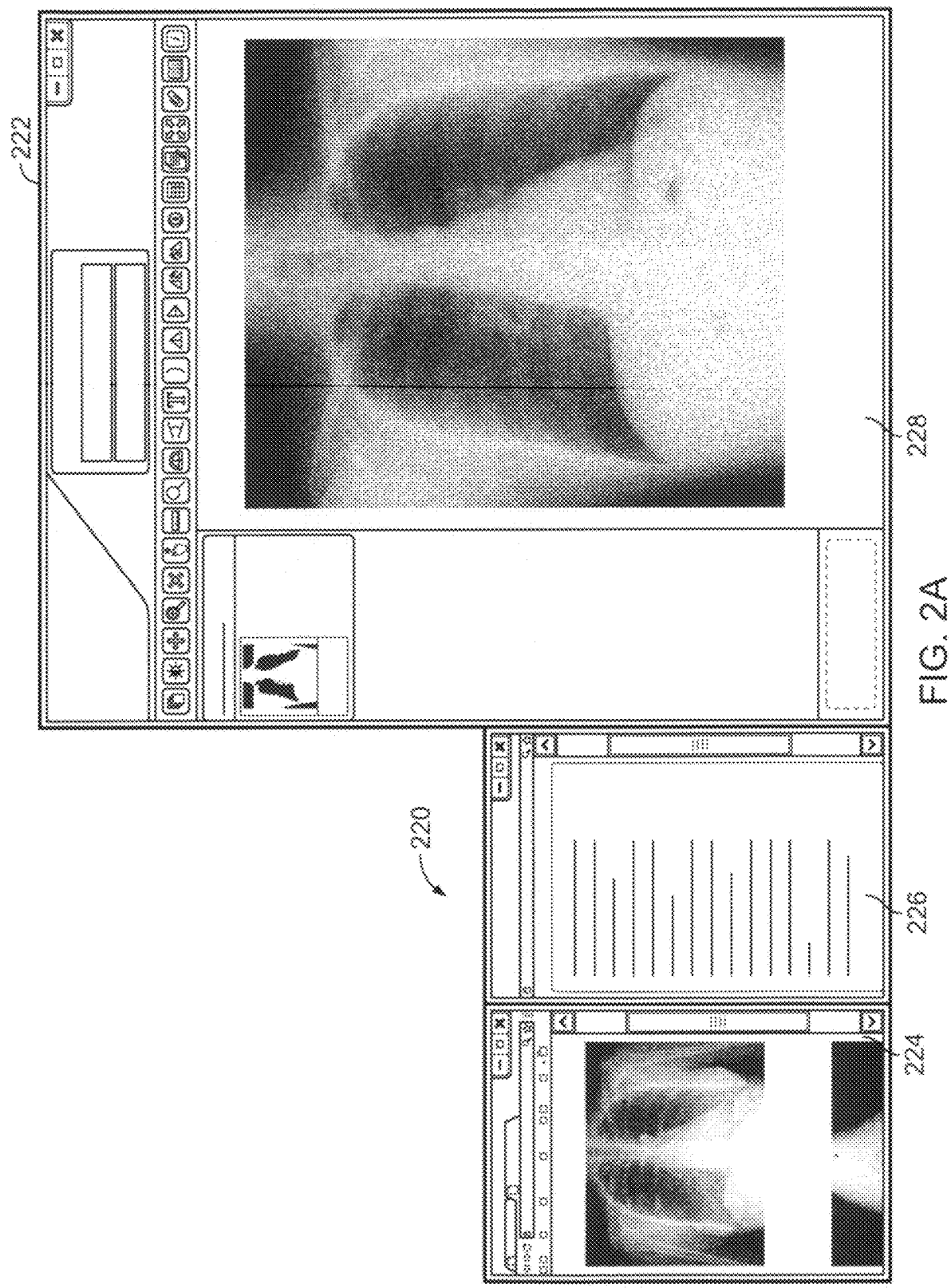
FIG. 2A is a screen shot of two screens simultaneously displaying three interfaces.

As shown in FIG. 2, the interfaces 202, 204, 206 of the viewer(s) 116, the decision support system(s) 120, and the active template(s) 118 can be displayed on a screen 200 of a user system simultaneously. Sometimes instead of three interfaces, a user may choose to display only one interface or two of the three interfaces simultaneously. Sometimes the three interfaces can be displayed on two or more screens, e.g., screens that are arranged side by side. The three interfaces can be displayed in different left-center-right orders than that shown in FIG. 2. An example of the display is shown in FIG. 2A. A viewer interface 228 is displayed on a screen 222, and an active template interface 226 and a decision support system interface 224 are displayed on another screen 224 arranged left to the screen 222. The screens 222 and 224 have different sizes. However, they can also have the same size.

In some implementations, displayed content(s) of one interface can be dragged and dropped into another interface, which can automatically update its contents based on the dropped content(s). In some cases, the features of two or all three of the interfaces can be combined and presented in a single interface to the user. In such cases, the features that we describe here can still be presented, but they need not be segregated formally among two or three different interfaces. For example a structured report can summarize the state(s) of the subject and contain links to any or all of the three primary interfaces used in generating the structured report.

The viewer interface 202 can be a browser window which functions to present visual representations (for example images) of the structured content to the user for the user to view, understand, and act on. The viewer system 116 is engineered to present DICOM compliant image data 208 (including images and related data) along with tools 210 through the viewer interface 202 to a user. The viewer system 116 can serve webpages, deliver images, and interact in other ways with the browser running on the user system in order to enable the viewer interface to provide the features that we describe, and others. The browser (for example a Google Chrome browser) can take advantage of HTML5 features including the recent "canvas" element, for example, to quickly download the image data (that represents the image) and store the image data in the user system running the browser. One advantage of downloading and storing the data on the user system is that the downloaded image data can be manipulated at a higher speed locally than could the image data if it were only remotely stored at the database(s) 114. In other words, the browser can manipulate the display of the image quickly for the user and therefore make the user experience satisfying.

The tools 210 enable the user to manipulate, change, analyze, measure, alter, and otherwise work with the image data and the image. Each of the tools can be context sensitive so that for different image data 208, different image capture modalities, different subjects, and different active template data, different tools are presented or the same tools may be presented differently with different features. Using the tools, a user can manipulate the image data 208, e.g., obtain various visualizations of image findings and/or make measurements of sizes or other characteristics related to the images, e.g., angles, attenuation, volume, etc.

The decision support system 120 runs on the server using decision-support data in the database, can present information related to the decision-support data through the browser of the user system, and can receive information from the browser of the user system, manipulate, and store it in the database for later use. The decision-support system can aid a user to make decisions or medical findings about (for example, to classify structured data about) a medical state of a subject whose medical data is studied through the viewer 116. The decision support system 120 includes a knowledge base that contains both static knowledge and dynamic data. The knowledgebase can reflect the knowledge of subject matter experts (SMEs) about medical conditions of subjects. The decision-support system interface 204 displays selected data and images from the decision-support system database, e.g., upon a user's choice, to the user.

The static knowledge is stored in the system 120 when the system is initially constructed or from time to time by updating the system. Examples of static knowledge include knowledge related to different subject matters, e.g., anatomy, normal and abnormal findings, normal ranges related to measurements, age of subject, position of finding within an anatomic structure, etc. Dynamic data is data added to the system 120 during the use of the decision support system 120. For example, data can be added into the system 120 based on images, e.g., anonymized images, that represent examples of normal and abnormal findings identified by the users. Generally, the knowledge stored in the decision support system 120 is input or confirmed by expert(s) in related field(s), and can help users of the system 120 to perform tasks, such as classification, using best practices.

In some implementations, the knowledgebase includes known ranges that are incorporated in element(s) of any one or more of the three interfaces. For example, specific pathologies may correspond to a known age range or known gender. The systems can automatically check the ranges against a subject's information to determine whether a user made a wrong classification or automatically exclude certain classifications. In an example of an active template having ranges incorporated, a template choice element, which can be in the form of an object, can have an age range attribute that limits the application of the template choice to only those subjects whose ages are within the incorporated range of the pathology. A user would be warned if he/she chooses a fracture only seen in pediatric patients when the patient is over 18 years old, when the age range is incorporated in the active template and associated with the fracture.

In an example of incorporating ranges in a decision support system, image examples, e.g., in the form of objects, representing a pediatric only fracture can incorporate an age range attribute such that if a user drags any of the image examples into the active template for a patient older than 18, the systems warns the user against using that specific example in that patient's report.

In an example of incorporating ranges in a viewer, a "Kline line" measurement tool can have age ranges incorporated for identifying a pediatric Slipped Capital Femoral Epiphysis (SCFE). If a user tries to use the tool on a non-pediatric hip, the systems warn the user of the improper use of the tool.

Information in addition to ranges, such as gender, ethnicity, etc. can be similarly incorporated to assist the user to make classifications using best practice. Such information can be incorporated in all systems/interfaces and all the interfaces are integrated to allow best practice.

The active template interface 206 can enable the user to use template(s) maintained and served by the active template system 118 to make choices and selections of elements of uniform descriptive information that are intended to be representative of a determined state of a subject. A complete set of choices and selections that has been made using an active template can be considered a classification of the state of the subject (for example, a diagnosis in the case of a medical subject). In that sense, the person who is the user makes use of the active template in operating as a human classifier. Once a complete set of choices and selections has been made using an active template, the data that represents the choices and selections can be stored locally and at the server and used for a wide variety of purposes and distributed to a wide variety of recipients. For example, using a classic approach, the choices and selections can be automatically expressed as a medical report on the medical state(s) of patients. The report could be distributed electronically or on paper and used in a conventional way. In another example, the systems can automatically classify a medical state of a subject to conform to statutes and other classifications, such as ICD-9 and ICD-10. The medical report can automatically contain the standardized/statute-compliant classifications/coding. In some implementations, the standardized classifications of the medical states are enabled by associating those classifications as attributes to the active template elements that denote their possible presence in the subject. The association can allow the medical report generated based on the active template to be automatically translated into the standardized classification/coding system. For example, sinus disease has an ICD-10 code. This code is associated with the active template element(s) that leads to the finding of sinus disease. As a result, a user's selection of the template element(s) not only leads to the finding, but also the standard coding of the finding.

The interface 206 can display an active template provided by the active template system 118 as a number of dynamic series of display elements (such as words or numbers and alternative words and numbers) such that each of the series potentially represents a set of syntactically correct sentences associated with an aspect or feature of the state of the subject. The set of sentences represented by one of the dynamic series can describe the vast majority of (or all of) the findings that might be present on a specific study of the image or other structured content. Example of a specific study could include a modality body part related study, e.g., X-ray for chest, CT for abdomen, etc., for a given subject.

The active template system stores program objects that represent words or numbers that can be presented in display elements as parts of the dynamic series of display elements that go together to form the potentially large set of syntactically correct sentences associated with various features of the state of the subject. The program objects stored by the active template system are based on knowledge imparted to the system by one or more subject matter experts. In other words, the program objects capture information from experts that can then be presented through the active template and used by a non-expert user to classify the subject and learn about appropriate classifications given underlying structured content about the subject and information presented in the decision support system.

In the example of a radiology study, the template system 118 can therefore include what amounts to a routine checklist or way of analyzing the subject of a SME, e.g., a trained radiologist. The template system 118 incorporates the knowledge of a subject matter expert and allows the active template to incorporate best practices in use of terminology, order of report findings, appropriate descriptors, and accurate classification. A user can activate and use the expert knowledge through the template interface 206 simply by interacting with the display elements. Interacting with the display elements can include clicking (or image drag and drop) on them making choices among alternatives, viewing tips, and observing the expansion and contraction of the number of elements included in the sentence comprising the elements, among other things. The template served by the template system 118 can also allow a user to readily choose and use complex tools in the viewer interface served by the viewing system 116 to make findings (choices, selections, Classifications) with the assistance of the decision support system(s) 120 and the template(s) 118. As a result, a generally trained medical professional who is not specialized in the subject matter of a particular study can produce an expert level report using the system 100. In some cases, even a relatively untrained person can use the system 100 to produce an initial reasonably good classification and related report.

The system 100 not only allows the user to classify the state of the subject accurately, quickly, and easily, it also provides a mechanism for acquiring, storing, and imparting to the user knowledge of a variety of subject matter experts. The knowledge is imparted in a simple, easy to understand, and smoothly integrated way that enables the user to take advantage of it, and to learn during the process of classifying the states of specific subjects. The expert knowledge can be presented through the decision support system interface and the active template interface, which both can work in an integrated way with each other and with the viewing interface. In the course of making selections, and choices in the active template interface, the user is prompted to consider information that represents knowledge of subject matter experts and is selected and presented in a way that is relevant to the context in which the user is working.

In addition, the user can learn and can be managed based on specific feedback provided with respect to classification work on the states of individual subjects. The feedback can include feedback that is provided automatically by the system based on data about similar subjects, similar states, and expert knowledge. The feedback can also include specific non-automated feedback provided case-by-case. For example, an expert can review a report produced by the user and provide direct or indirect feedback indicating where errors were made, for example.

The feedback can be automatic feedback. For example, when there is a discrepancy between the reports of the expert and the beginner, the beginner can review a redline version of the report, in which where the expert report differed from the beginner report has been automatically noted. This review can be prompted in real time once the expert is done with evaluating the subject. The systems can also automatically generate an excellence score for the beginner by comparing the reports of the expert and the beginner and adding up the level of mistakes related to the value of the attributes. The mistakes can include both false positives and false negatives.

In addition, parties who have access to information that establishes the actual state of the subject can provide that information to the user, sometimes after the fact. For example, a surgeon who removed a cancerous section of a colon from a patient and who observed the actual extent, severity, and character of the malignancy can provide direct feedback through the active template system to the user indicating the actual state of the subject. In addition, this actual state information can be used in connection with the structured content as a basis for improving the underlying data stored in the system. For example, information of the actual states can be loaded into the systems automatically to improve the data in the systems so that veracity of specific pathologies is effectively crowd sourced. In some implementations, the information of the actual states, e.g., surgical/pathological data can be automatically correlated to specific images/subjects, e.g., be noted as an attribute of an image, in the decision support system. The information can then be used as a surgically/pathologically proven case of a specific state of a later subject image/study.

In some implementations, a less skilled pathologist, for example, located in a part of the world where the general skill of pathologists is lower than in another part of the world, can provide useful classifications and related reports about subjects, and then the reports can be quickly reviewed, critiqued, adjusted, and issued by a more skilled pathologist located in the other part of the world. A wide variety of other use cases are also possible.

Examples

When the system 100 of FIG. 1 is for use in medical diagnosis based on medical images, the viewer is browser-based and DICOM-compliant and programed to be native with respect to a given browser, such as Google Chrome. In some implementations, the viewer uses features available in HTML5, such as the canvas features, to view diagnostic quality, DICOM compliant images. Diagnostic quality images typically follow the guidelines offered by the American College of Radiology. The Federal Drug and Food Administration (FDA) regulates imaging devices and some imaging devices that produce diagnostic quality images are FDA approved (401k). The viewer makes use of the browser capabilities to store the images on the local hard drive for rapid retrieval by the user.

When images of a subject are to be studied by the viewer, instead of the actual subject, the system 100 receives the diagnostic quality, DICOM compliant images from various client sources and provides reports to the client sources. The DICOM standard includes the method of sending images to the system 100. Generally, all imaging devices throughout all medical specialties, including radiology, pathology, ophthalmology, GI (Colonoscopy), etc., manufactured since 1990 have the capability or can be enabled to have the capability to send DICOM images to a DICOM destination over TCP/IP. A DICOM destination includes 3 pieces of information: (1) the Application Entity Title, which typically has 16 characters, (2) the IP address, which can be the standard 4 block IP address or a domain name, like dpr.lifetrackmedicalsystems.com, and (3) the port over which the information is sent, which typically is port 104.

A new client of the system 100 can be readily added to the system 100 for uploading images and access the system. For example, the system 100 can provide an approved new client with the information (1)-(3) of a server on which the system 100 is operated. The new client then can enter the three pieces of information through a DICOM destination dialog box/interface of an imaging device that is connected to the internet. The device then can communicate with the server, which is a DICOM compliant destination. The destination IP address (or the second piece of information) is the internet (or LAN) location of the server which receives the DICOM images, which can be a server located in the Singapore Amazon Web Services (AWS) datacenter.

Other than the clients, users of the system 100 also include readers of the images who generate the reports for the clients. Eligible readers may include radiologists or other medical professionals. The readers can review the images using a processor/workstation local to the LAN based onsite server of the system 100. The readers can also review off the WAN based server of the system 100, e.g., the Amazon Web Services (AWS) based server, e.g., through the Internet, or off a mirror server that is a mirror of the AWS WAN based server of the system 100. The mirror server can be set up at a location different from the AWS server of the system 100 and can allow faster image retrieval by onsite readers since it is on site and images are retrieved to local workstations over the office LAN. For example, the mirror server can be located on the LAN where a readers' workstation exists and can synchronize with the server of the system 100.

The system 100 is highly de-centralizable and can receive input from radiologists working from home with an inexpensive, low cost, e.g., less than $1,000, processor-based workstation. The workstation is capable of acting as an "acceleration server" which pre-fetches studies assigned to a specific radiologist. The radiologists working for the system 100 can be located anywhere in the world, e.g., anywhere that has consumer bandwidth (1-5 Mbps) connections to provide highly efficient radiology reading services.

The system 100 can allow a client to store and archive images locally on the LAN of the client. The client can host a server with the system 100 at the location of the client, e.g., a hospital or an imaging center. For example, a client hospital or imaging center may want to have a mirror of the entire system located on site in the event that internet access is unavailable intermittently. The server hosted by the client can also mirror all the same information on the server of the system 100. The images in the system 100 can be archived both onsite on the client LAN and on the server of the system 100, e.g., by using Amazon S3 (Simple Storage Solution) hard drives. The client can access all studies and reports even if the internet is temporarily unavailable to access the server of the system 100.

In some implementations, functionally, the client owns the images and the system 100 owns the active templates and the decision support system(s). The system 100 can also own all data related to the active templates and the decision support system(s), and can contractually own the anonymized images that are added to the decision support system(s).

In some implementations, referring to FIG. 3, when a user logs into the system 100 through a browser, a worklist 300 is displayed through an interface 301 to the user working on a user system. The worklist provides a list of records 302, 304, 306 for the user to view. Users who have may have different roles with respect to subjects, e.g., nurses, doctors, or administrators, or users of different entities, e.g., hospitals, have different permissions to see different records. The levels of permissions are encoded by the system 100 in association with the user's registration to the system 100. The display and access of the records are in compliance with the HIPAA Privacy Rules. From the list of records, the user can choose one or more to review, alter, critique, conduct a study, or perform other functions. In this example, the user's user name 342 and role 340 are listed in the interface showing the worklist 300. Additionally, the institution 344 to which the user belongs is also listed.

In this example, the worklist 300 shows three records 302, 304, 306 in the form of a table. The table has multiple fields that differentiate and/or summarize certain aspects of the different records. For example, the fields include patient name 308, patient ID 310, accession no. 312, institution name 314, modality 316, body part 318, #SE (number of image series)/#I (number of total images in the study) 318, study date 322, received date 324, description 326, QA (quality assurance) status 328, and status 330.

The patient name and the patient ID identify the subject of the medical record. The patient ID is a unique ID for each patient within the system 100. The accession number is a unique number associated with a study ordered at an imaging center. The institution 314 specifies the origin of the medical records. The modality 316 is the type of image capturing technique used, such as magnetic resonance imaging (MRI). The body part 318 identifies the part of body for which medical images are recorded. The SE 320 is the number of series, the #I is the number of total number of images in the study. The study date 322 shows the time at which the records are studied. The received date 324 records the time at which the records are received by the system 100. The description 326 provides a brief description of the records.

The status 330 shows the status of the report to be generated or generated from the study of the corresponding record. The status can be "new," "submitted," "verified," "dictated," "preliminary," and "final." The status of "new" means that the corresponding record or case has not been reviewed or reviewed all the way through to generate a report. The status of "submitted" means that the client who sends images to the system 100 has determined that the record is ready for presentation to a reviewer, e.g., a radiologist. The status of "verified" means that the record indeed has been verified, e.g., by nurses of the system 100, that a record contains all appropriate information for the initial reviewer to review. The status of "dictated" means that the initial reviewer has made their initial classification/report. The status of "preliminary" means that a second classifier/reviewer/advanced reader has reviewed the record and the initial report generated by the initial reviewer and has made changes to the initial report. The status of "final" means that the report is signed and placed by the classifier/reviewer/radiologist of record.

The attributes of the status 330 can be named differently from the above discussed names. In addition, there can be other statuses, including medical statuses, financial statuses, or procedural statuses of patients. The worklist 300 can have fields related to a radiology information system (RIS). For example, the worklist 300 can include additional fields for patient scheduling and billing. The worklist 300 can also include derived fields, e.g., fields automatically generated by an active template, such as ICD-9/10 codes, conspicuity and severity values, and intelligent user efficiency related time stamps. Specific examples of derived fields can include time of image receipt to time of final report (i.e., turnaround time), and attributes related to the reports, e.g., the ICD-9/10 codes and CPT (Current Procedural Terminology) codes. Generally, the CPT codes are related to an actual imaging procedure which can be determined by a radiologist noting which views and series have been performed. For example, a two view chest has a different CPT code than a single PA view. The system 100 can automatically determine the CPT code, e.g., based on the selection made at the active templates. For these examples, the worklist 300 can include statuses of the patient scheduling and billing, the turnaround time, and the attributes related to the reports.

The RIS contains information related to patient demographics, scheduling of studies and billing, and patient tracking, e.g., when a patient arrives in the imaging department, when the patient leaves, whether it is inpatient or outpatient, information related to report distribution, including primary care physician, ordering physician, consulting physician(s), referring physician, primary reading physician, second reader, CPT and ICD-9/10 codes, etc.

The QA status 328 is a custom, non-DICOM field for noting if there are quality assurance issues, e.g., with the records received from the client. The QA status may indicate that such issues exist and the system 100 or a user of the system 100 may request the client to address the issues in order for the user or other users to process the record and generate a report based on the record. For example, if the client, e.g., an imaging site, informs the system 100 that two views of a chest have been sent to the system 100 for an X-ray study, while the system 100 only receives one view, the system 100 or a user of the system 100 places a note for the missing view in the QA status 328. The note in the QA status 328 can be in the form of a QA code for easy searching. Also, the placement of the note sets the status 330 in a "New" status and notifies the client to address the QA issue. In the example discussed above, the client can address the QA issue by sending the missing or by changing information about the number of views, e.g., header information, to match the available views.

In some implementations, an authorized user may add additional fields to the table. Sometimes a user is not interested seeing in all fields and can click on a hide button 380, e.g., to hide the QA status field 328. In some implementations, the system 100 allows a user to show or hide any one or more fields so that the user can define his/her own worklists. The user can perform functions on any of the shown fields and/or filtered fields, which can include any attributes of the fields, including those derived from the active templates, e.g., the ICD codes. Field filtering is described further below.

When the worklist 300 contains multiple pages of records, a user can use the button 392 or the button 398 to reach the first or last page of the records, or can turn pages of the record back and forth using buttons 394, 396.

The system 100 allows a user to invoke a field filter on the worklist 300 to build customized worklists from the worklist 300 based on the user's needs and perform functions on the built worklists. The records in the worklist 300 can be sorted or filtered based on the contents of the fields. The sorted or filtered records may provide a user with information, e.g., statistical information, about the records or patients. Each field of the record includes an activatable button 350 that shows a sorting standard, e.g., alphabetical sorting from A to Z or from Z to A. Some activatable buttons for some fields can have more advanced sorting standards. For example, for the institution name field 314, in addition to the alphabetical sorting, an additional filter 352 is provided, e.g., popped up in the interface. Referring to FIG. 3A, as an example, the pop-up window 354 contains selectable phrases 356, 358, 360, 362, 364, 366 and an open field 368 for a user to fill in. The combination of the selected one or more phrases and the content filled in the field 368 can form a filter string. The user can choose to apply the filter string by activating an apply button 370 or delete the filter string by activating a delete button 372. The pop-up 354 can be moved within the interface 301 and can be closed by activating a close button 390 on the pop-up. In addition, a user can search the records by entering search strings in a search field 382. In some situations, search is functionally a form of filtering supplanted by the field filter functionality.

Filtering can be performed on any field of the worklist 300, including those fields that are hidden or derived, and those fields that are automatically encoded by one or more active templates, e.g., the quality/conspicuity data encoded as attributes in the elements of the reports generated by the active templates, and the ICD-9/10 and CPT codes. By defining the fields of a worklist, including the hidden fields, and then filtering on these fields, including the derived fields, a user can generate a worklist based on his/her needs. For example, a worklist that includes only MRI brain studies greater than one hour old and received from a specific institution can be generated from a general worklist of the system 100 that includes much more information. The user can perform one or more functions on the generated worklist by invoking the field filter function. For example, using the field filter function, a user can find out which cases/records have not been read in a timely manner and can notify a hospital administrator and a radiologist to read these delayed cases/records.

In some implementations, the field filter function capability of the system 100 can be viewed as a form of language when used in conjunction with the general worklist, e.g., the worklist 300. The application of filters on worklist fields can create highly customized worklists (which can be viewed as nouns) upon which specific functions (which can be viewed as verbs) can be performed. The application of a function in a worklist is analogous to applying a verb to a noun to create unique and powerful combinations intuitively. Applying filters on fields creates unique worklists which can be viewed as the equivalent of nouns. This language can provide a powerful, intuitive paradigm in which filters acting on fields to create custom worklists "nouns" in an intuitive manner. Specific functions (verbs) can then act on these custom worklists to cause powerful and intuitive actions to occur on specific subsets of the worklist information. For example, in the institution name filter shown in FIG. 3A, a user can filter on a field using functions including "is," "is not," "contains," "does not contain," "begins with," "does not begin with," etc. (not all shown). In the example of time fields in the worklist, the filters can be applied to dates and/or times, e.g., "is less than" or "is greater than" "X hour(s)/days/weeks/months/years," "is done" or "is not done" on specific date(s), date range(s), etc. Application of the field filters can generate useful and highly specific worklists based on the needs of different users.

The users and/or the system 100 can then perform functions on the generated worklists. Examples of the functions can include notifications to hospitals, radiologists, or other individuals/entities using, e.g., short message service (SMS), email, phone call, etc.; and Excel/comma delimited export of the data in the generated worklists. Users, e.g., administrators, can determine patient throughput from the exported data, and radiologists can determine their own efficiency and quality or similar data on others.

A user can choose one or more of the records for study/review by clicking on the patient name in the patient name field 308. The activation of the patient name causes a display of the medical information stored for the patient. In some implementations, the activation directly leads the user to a viewer interface in which medical images are displayed in a viewer. A user may also access a viewer interface by clicking on a viewer button 384 on the interface 301. The activation of the viewer button 384 opens one or more viewer interfaces that include studies corresponding to those records having the check boxes in the leftmost of each record checked. One or more studies can be simultaneously opened. In addition, medical reports generated for the records can be viewed by activating the status of the report in the status field 330. A user can further access active templates from the report(s) (see, description of FIG. 4 below). As described previously, the template(s) and the viewer(s) can be simultaneously displayed to the user through multiple interfaces.

The values shown in the cells of the table are populated from information stored at the server in the database.

Figure 4:
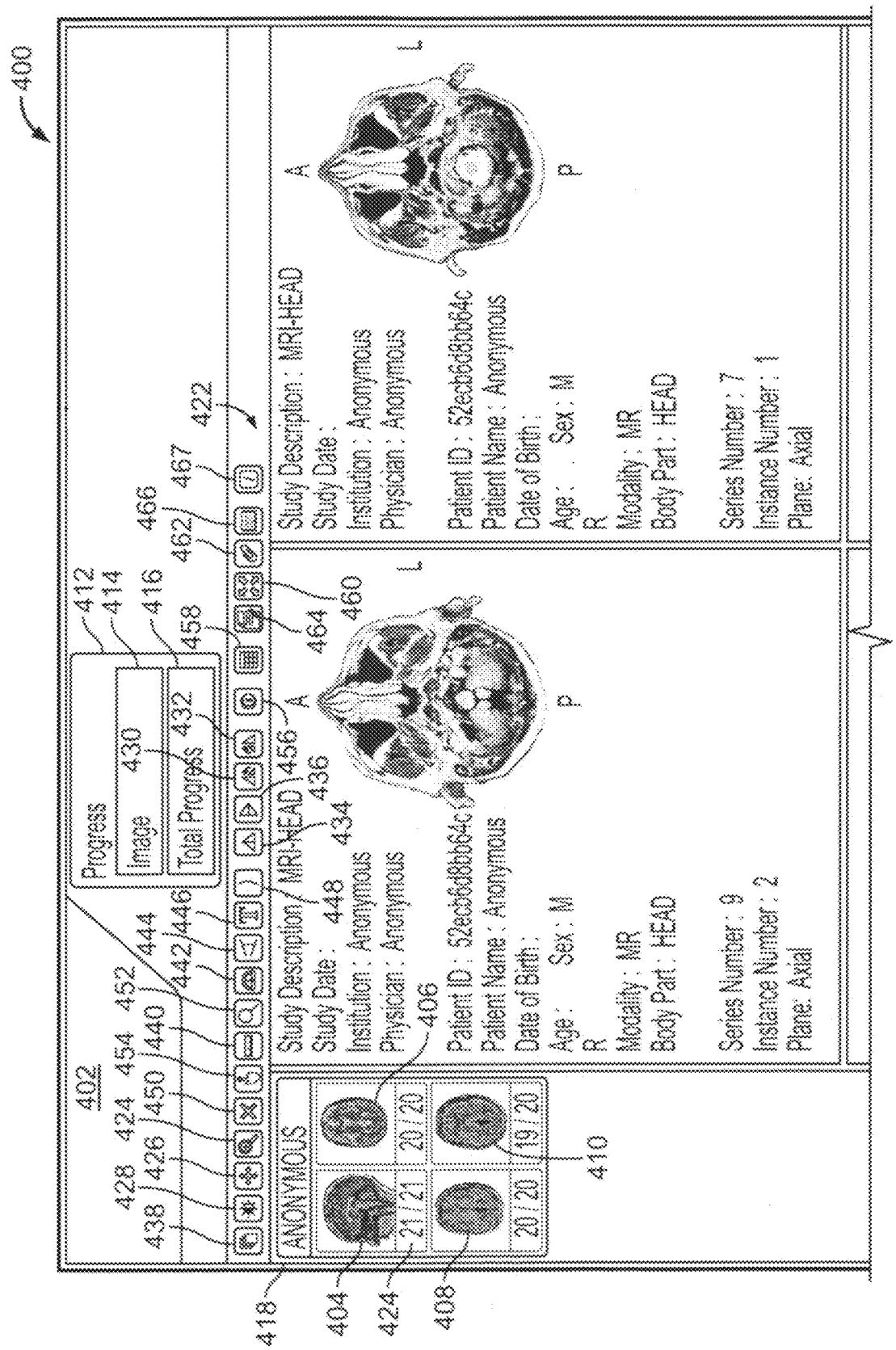
FIG. 4 shows an example of a viewer.
Figure 4:
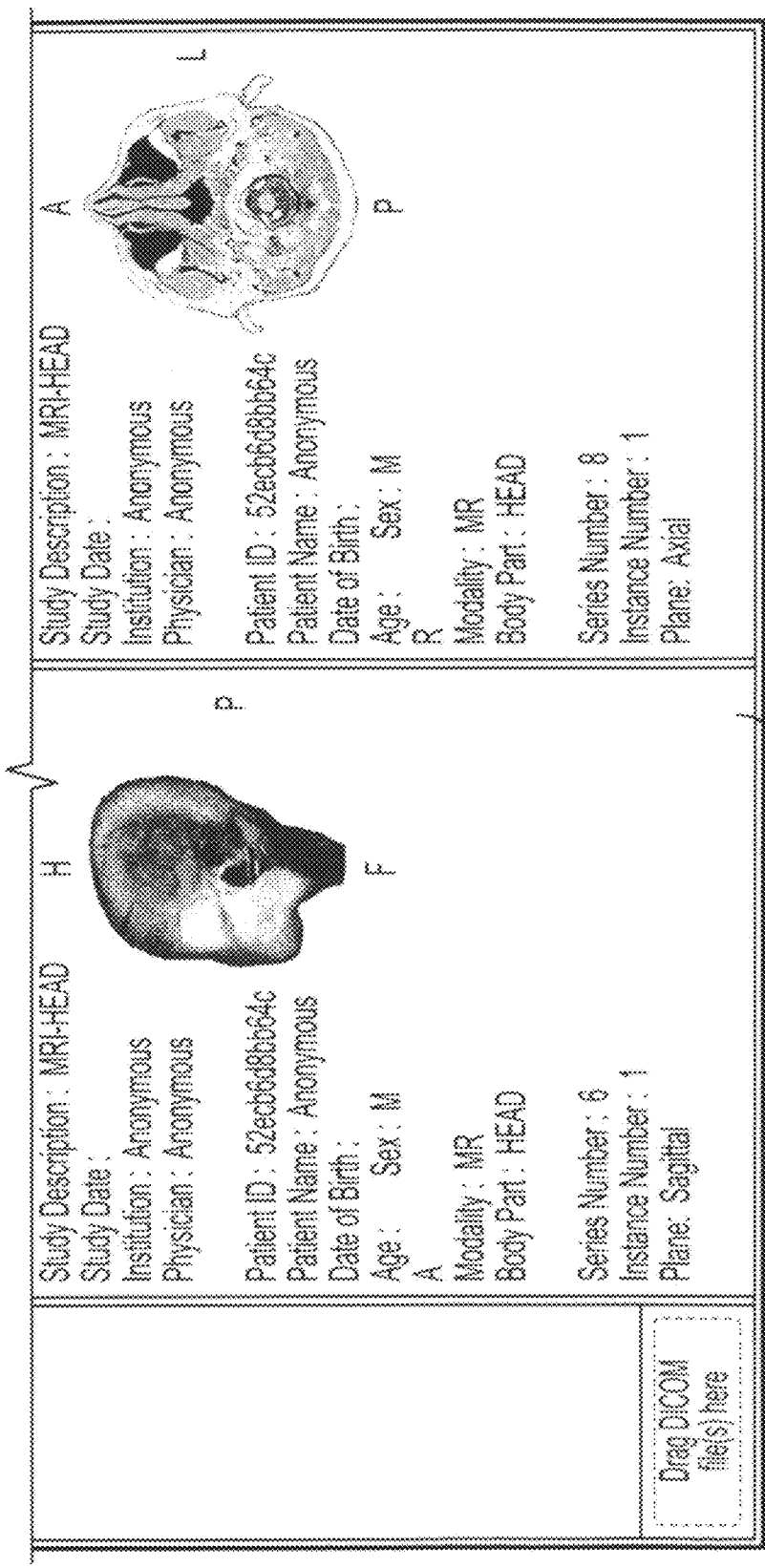

Referring to FIG. 4, a viewer 400 is displayed through a viewer interface 402 presented by a browser to a user when the user chooses to study a record of the worklist 300 of FIG. 3. In this example, the user clicked on the patient name of the record 306, which contains medical records of MRI performed on the brain of the patient. The viewer 400 includes a record region 418 in which medical images, e.g., MRI images of the head, are displayed in a thumbnail form. The viewer 400 also includes a working field 420 into which one or more of the MRI images in the region 418 can be dragged and dropped for detailed analysis. Although four images are shown in the working field 420, when the viewer is open, the working field is empty and the images can be added or removed from the field 420. In addition, the viewer 400 includes a set 422 of tools for use in analyzing the images.

When the record is first-time selected, the selection initiates a downloading process for the MRI images 404, 406, 408, 410 and all available tools from the server/database of the system 100 of FIG. 1 to the local hard drive of a user system on which the viewer interface 402 is run. A viewer code base associated with the downloaded images and the tools can be stored in the browser cache. As a result, when a user makes subsequent accesses to the viewer 400, the downloading does not have to be repeated. When one or more features of the viewer or the system 100 are updated, a user can clear the browser cache and reload the browser to effectively upgrade the viewer and the system 100 accessed by the user through the browser.

The progress of the downloading are shown to the user in a progress window 412, which includes one image bar 414 and one total progress bar 416. During the downloading, the bars are dynamically filled to indicate the downloading progress. The image progress bar 412 shows progress of downloading the current image only, whereas the total progress bar shows the progress of downloading the entire study. In addition, the downloading progress of each individual image is shown in a corresponding bar 424 under each thumbnail image. The bar 424 contains two numbers, one in front of a slash and one behind of the slash. The number in front of the slash shows the number of images available on the local hard drive of the user out of the total number in the series denoted by the thumbnail. The number behind the slash indicates the total number in the series represented in the corresponding thumbnail. The number in front of the slash increases from 0 during the downloading and when the downloading is completed, the number equals the number behind the slash, thus identifying when all the images in the series have been loaded to the local hard drive. In some implementations, the color of the bars 414, 416, 424 can turn green to indicate completion of the downloading. The viewer 400 is configured such that the downloading process takes only a short period of time, e.g., less than 10 seconds, less than 5 seconds, or less than 1 second. Different images and tools can be downloaded simultaneously.

A user can use the tools in the tool set 422 to manipulate the images in the working field 420 to measure characteristics of the images and to annotate the images and their characteristics. Example manipulation tools include but are not limited to: magnification tool 424, pan tool 426, window level tool 428, rotate tools 430, 432, flip tools 434, 436, scroll or browse tool 438 for scrolling or browsing through a stack of images, e.g., in CT or MRI, invert color tool 456, view point selection tool 458, full screen tool 460, and drag and drop tool 462. Example measurement tools include but are not limited to: linear distance/size tool 440, volume tool (not shown), and Hounsfield units tool 452, e.g., for measurement of x-ray attenuation, which can roughly be electron density of matter, and angle(s) 442, 444. The measurement tools can also include any number of context sensitive measurement tools that are automatically chosen through the use of the decision support system(s) and the active template(s). For example, for MRI studies, spine disc bulge measurement tool(s) can be automatically chosen and shown when reading an MRI of the lumbar spine, or in a calcaneus fracture when the user identifies a definite or possible calcaneus fracture the Boehler's angle measurement tool(s) can be automatically chosen and shown. Example annotation tools include but are not limited to: text tool 446, label tool 448, removal tool 450, and annotation manipulation tool 454. In addition, the tool set 422 also includes a button 464 that allows a user to access the report editor and active template(s), a button 466 to access the decision support system(s), and an information tool button 467, the activation of which shows a user the DICOM header information of the study.

The tools are shown in the interface 401 in the form of icons that graphically explain the use of the tools to aid a user in using the tools. To facilitate the usage, when a user moves a mouse or figure onto an icon, a brief explanation of the icon and the tool appears on the interface. Activation of a selected tool allows the user to apply the tool in the viewer 400. Additionally, a tool can also function as an object that has attributes, which includes showing an appropriate portion of the decision support system to provide a user with detailed information on the use of the tool. For example, the detailed information includes the significance of the tool in the classification of the subject under examination. The attributes of the tool object can also be related to information contained in the study, e.g., the patient age and gender, such that a user using a tool that measures the volume of the ovaries to study a male patient is warned.

The tools shown in the tool set 422 with the images for a particular study can be sensitive to the context of the study. In some implementations, the use of specific tools is encoded in the tools based on information known to the system 100. The information can include contents of the images, and/or contents of the other interfaces, including interfaces displaying the active template(s) and the decision support system(s). For example, the information includes the modality, and/or the body part, and/or the client, and/or referring physician, and/or reading physician of the images to be studied. In some implementations, the tools are related to one or more active interactions the user made with the active template(s) and/or the decision support system. For example, specific selections of choices or modifiers from the active template(s) and selection of diagrams, images, or text elements from the decision support system can affect the tools. The details of these templates are discussed further below.

In some implementations, a user can encode the tools, and by encoding the tools, a user can use specific tools as desired. For example, the client is a podiatrist and may want all of his/her foot films to have multiple specific measurement tools used on all foot radiographic studies regardless of whether there is a determination of normal or abnormal. A tool can also be encoded automatically by the system 100 to help discourage inappropriate use of the tools and encourage appropriate use of the tools based on the attributes of the tool. For example, a tool may be encoded such that the tool is to be used on calcaneus only, or is to always measure a volume of the ovaries on a pelvic ultrasound of a female. In addition, a tool can be encoded such that the tool is triggered by clicking on an image or diagram from the decision support system. For example, the image of the decision support system can be associated with the use of a specific tool such as Boehler's angle on a calcaneus fracture or Kline's line on a pediatric pelvis being evaluated for SCFE (slipped capital femoral epiphysis).

As a result, the integration of the RIS (Radiology Information System) with its knowledge of the patient and the images, in conjunction with the knowledge of the chosen elements in the active template(s), the system 100 can automatically inform a user which tool to use to make a specific measurement for the chosen elements. For example, the system 100 can highlight the tool in the toolbar and/or a popup can be generated on the viewer, if appropriate. In some implementations, when a user chooses a tool for use, the tool has been automatically encoded with the desired measurements or manipulation the user would need to apply. For example, in a calcaneus fracture, the Boehler's angle tool is automatically activated on noting the presence of a calcaneus fracture when an appropriate element in the active template is selected via mouse click or drag and drop of the image showing the fracture. With the Boehler's angle tool being active, a first user click on the image at the appropriate location determines an initial point of measurement of the angle. A popup can guide the user to perform the rest of the measurements. Alternatively, the system 100 can guide the user by having the appropriate information displayed on the decision support system.

In some implementations, a full set of tools in the system 100 may not need to be shown for particular studies, and different tool sets having different numbers or types of tools can be shown for different studies. For example, the Hounsfield tool used for a CT study is not shown for use on an MRI study. By not showing unnecessary tools based on content known to the system, the viewer interface is cleaner.

In some implementations, the tools contain normal values that correspond to the context of the study. For example, a tool for use in measuring the acromioclavicular distance can have a normal distance smaller than 6 mm as an attribute of the tool. If the measurement performed by the tool shows that the actual distance is larger than the normal distance, the user can be informed of the abnormality of the measurement, e.g., in a popup and. In some implementations, the system 100 can automatically preselect the active template elements that describe the abnormality. Additionally, a tool may have an attribute that adds the appropriate active template element that describes a measurement result by the tool, and/or that suggests the user of other tools. For example, the template element to be added includes acromioclavicular separation types, and the other tools include acromio-humeral distance measurement tools.

A measurement tool for measuring a feature in a particular study can be encoded with a value or a value range in which the feature is deemed as being normal and/or other functions as attributes of the tool. A measured value different from or outside of the normal values/normal value ranges encoded in the measurement tool can indicate that the feature is an abnormal medical state. Furthermore, the button 466 can guide a user to the relevant decision support system page describing the potential abnormal state to obtain examples of normal or abnormal values, images, and diagrams to facilitate the use of the tools. The user can be prompted to use other related tools to evaluate commonly associated abnormalities.

In some implementations, the system 100 automatically associates values obtained from use of the tools, e.g., the measured value(s), with the active template(s) of the same study and/or a report generated from the active template(s). The automatic association can be triggered by activation of a tool itself, or by a tool's context sensitive use in the study. For example, the system 100 can insert the values into structured reports when the drag and drop tool 462 is used to drag and drop an image with a measurement or annotation into an active template in a template interface displayed simultaneously to the interface 402.

In some implementations, when an image is moved from the thumbnail region 410 to the working region 420, the image is automatically annotated based on stored information about the image. The stored information can include information received with the records, e.g., from different institutions or individuals, information entered by administrator of the system 100, and information from the past use of the active template(s) and/or the decision support system(s). In the example shown in FIG. 4, the four images 404-410 in the working region 420 are annotated in text on a side of each image. The text lists the study description, study date, institution, physician, patient information including patient ID, name, date of birth, age, and sex. In addition, information about the image, including the modality, the body part, the series number, the instance number and the plane, is also listed. In addition, the plane in which the image is shown is automatically labeled. For example, the images 406, 408, 410 are in the axial plane and the four directions A—front, P—back, R—right, and L—left are labeled. In another example, the image 404 is in the sagittal plane and the four directions H—Head, F—Foot, A—anterior, and P—posterior are labeled. During a study, further use of the tools in the viewer, the active template(s) and/or the decision support system(s) can automatically and dynamically update the annotation. For example, when a distance between two points on the head is measured, description of the distance and its measured value can be listed.

As another example of the system 100 using its knowledge about the case to prompt a user to take the right steps in classification, when the user is reviewing a particular part of the body of a subject, e.g., the right shoulder, template elements for the left shoulder are grayed out in the active template so that the user does not mistakenly classify the left shoulder based on review of the right shoulder.

Example Active Templates

The active templates can facilitate a user to build a comprehensive medical finding report based on information presented in the viewer. Using the template(s), a user can diagnose a medical state of a patient in connection with the patient's record shown in the viewer, or determining/classifying the data of the record relative to baseline/normal ranges based on prior knowledge/aggregated data. The system 100 stores multiple model templates for use in classifying different studies. When a study based on a record starts, a user can access a database that stores the model templates and choose an appropriate one based on the context of the study, e.g., the content of images in the record. In some implementations, the system 100 uses the known modality and body part being studied in the viewer, which complies with the DICOM standard, to automatically load the correct active template, if it exists. When a study has been partially conducted or completed, an active template for this particular study has been saved in the system 100. When a user accesses the template to continue with the study, instead of the model template, the previously saved active template for this particular study is loaded and displayed to the user based on the system's knowledge of the study.

The user can access the database storing the active templates from multiple interfaces, e.g., the status column 330 of the worklist 300 in the interface 301 of FIG. 3 or the button 464 of the tool set 422 in the viewer 400 shown in the interface 402 of FIG. 4. In some implementations, a selection interface is displayed to a user, e.g., simultaneously with the display of one or more of the worklist interface 301, the viewer interface 402, and a decision support system interface (discussed below), to allow the user to choose a desired model template. In some implementations, when a study has been completed and verified, a user may directly access the report for the study, through which the user can access the active template and then generate the report.

Figure 6:
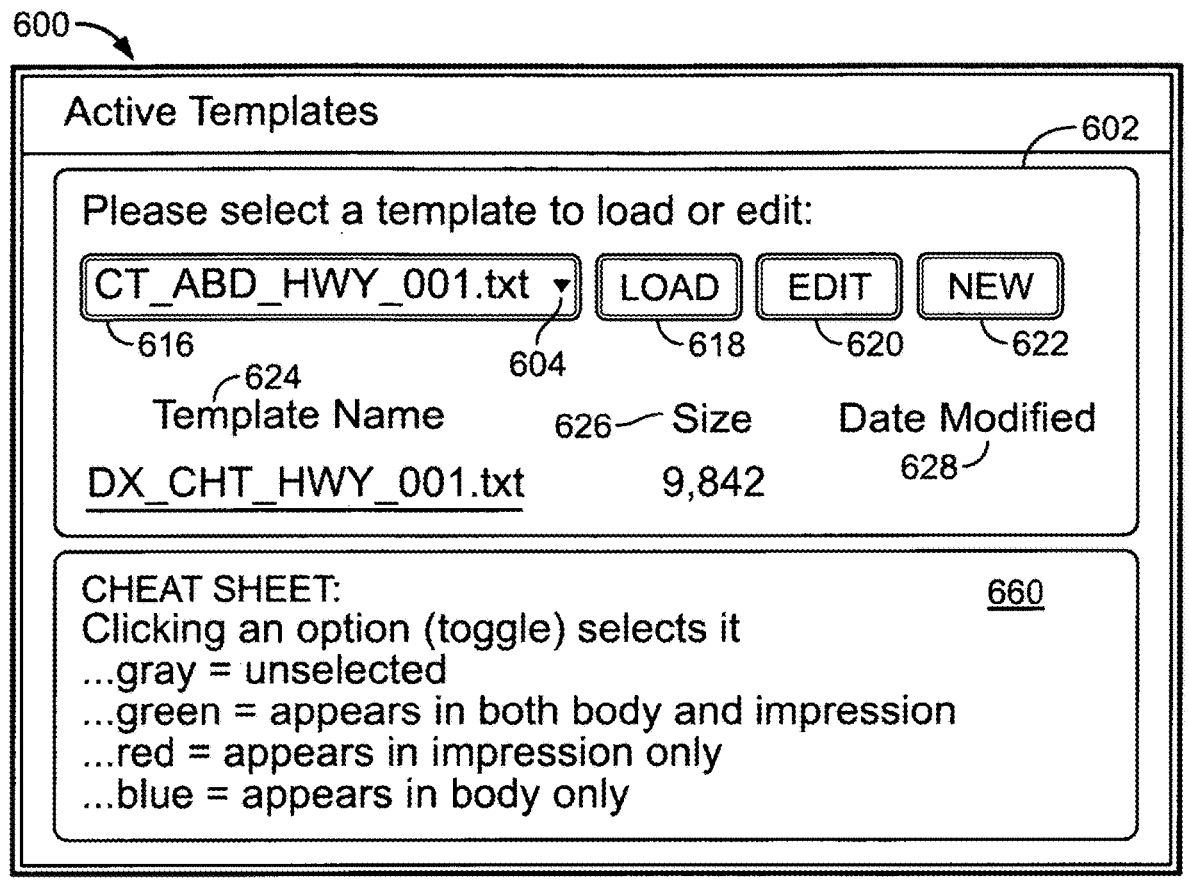
FIG. 6 shows an example of a template selection interface.
Figure 6A:
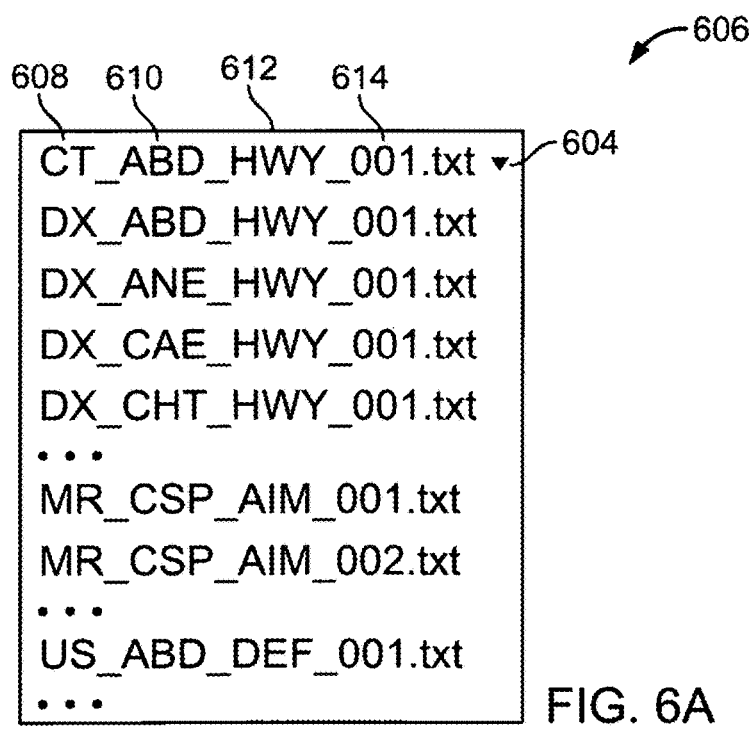
FIG. 6A shows an example of a drop down menu in a template selection interface.

An example template selection interface 600 is shown in FIG. 6. In a window 602, a user can view available template choices by clicking on a button 604, which shows a drag-down menu with a list of available templates. FIG. 6A shows an example menu 606. In this menu, the templates are named with three alphabetical strings 608, 610, 612 and a numerical string 614. In this example, the first alphabetical string 608 is a two letter code that complies with the DICOM standard for modality/imaging device. The code denotes the medical methods used in obtaining the medical records or images. For example, "CT" represents CT scan, "DX" represents diagnostic X-ray, "MR" represents MRI scan, and "US" represents ultrasound. The second alphabetical string 610 denotes the body parts on which the medical methods are applied. For example, "ABD" represents abdomen, "ANE" represents ankle either, "CHT" represents chest, and "CSP" represents cervical spine. The third alphabetical string 612 denotes the client/institution/generic template. For example, "HWY" represents Healthway, and "DEF" represents default. The numerical string 614 denotes any of 1000 or more variations of the templates to allow for potential variations based on referring physician, reading physician, and any other variable that may determine the most optimal active template. For example, "001" represents the first version of the active template and "002" represents the second version of the active template. Although the template choices are arranged in alphabetical order and the specific strings are used to name each template, the template choices can also be organized in different orders and different names can be used for the templates. For example, additional blocks, e.g., three letter blocks, can be added to the template names to represent language, country, physician, CPT (i.e., number of views), and etc. The templates can be named in as complex a way as a user might want.

The template selection interface can have other forms different from the interface 600 of FIG. 6. Another example template selection interface 660 is shown in FIG. 6C. The interface 660 is similar to the interface 600 and allows a user to select a desired active template from all active templates available in the system 100 in a window 662. Compared to the interface 600, the interface 660 contains additional information including the DICOM header information 664 and the current status 666 of the case/record. A user can change the status to dictated or submitted using buttons 672, 674 or save the status using a button 670. In addition, the interface 660 is incorporated in a report window 668, from which the user can access, generate, or cancel a report.

Although the template selection interface can be used by a user when necessary or when a user chooses to, the selection of the appropriate template can be automatically performed by the system 100. For example, the system 100 can choose a template based on the DICOM header information including the Modality, and the Body Part, the RIS which has the information on the Institution and User Login, etc. The system-chosen template can be automatically loaded and presented to a user, while the user has the option of choosing a different template through the template selection interface.

In some implementations, the system 100 stores a template for each known medical study of a body part so that a template is available for all conventional radiology studies of any body part (would likely use CPT code (which tells how many views) to select). The system 100 can automatically choose a template for a user to use, e.g., using the CPT code. A user can choose a desired template, when the automatically selected template is inappropriate or the user prefers a different template, by choosing one of the template choices, and the choice is then shown in a window 616. Information of the chosen template, such as template name 624, size, 626, and date modified 628, is displayed. The user can then load the chosen template by activating a "load" button 618 and use the loaded template for generating a report. The user can also edit the chosen template by activating an "edit" button 620. For example, when a user finds that the desired template contains error(s) or needs to be supplemented with additional elements, the user can access the source code of the template to edit the template.

Figure 6B:
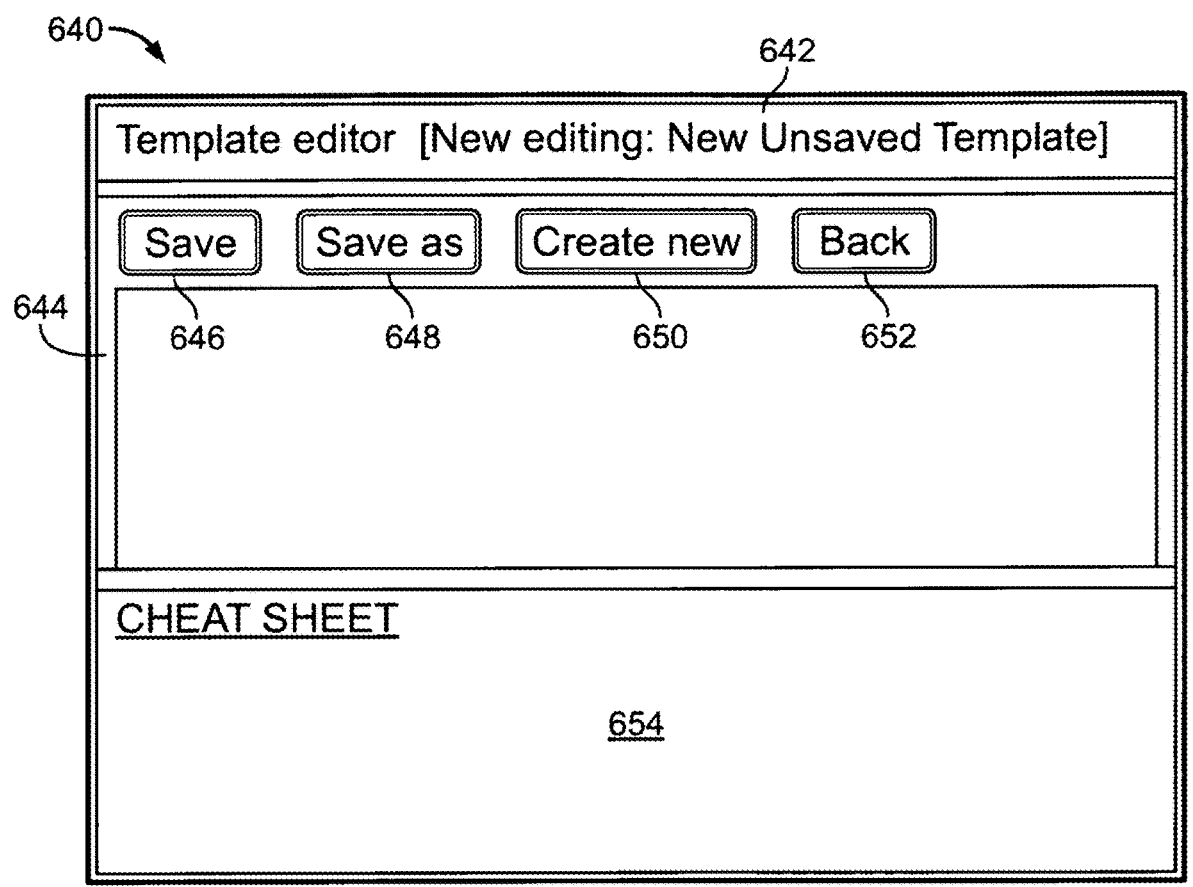
FIG. 6B shows an example of a template editor.
Figure 6C:
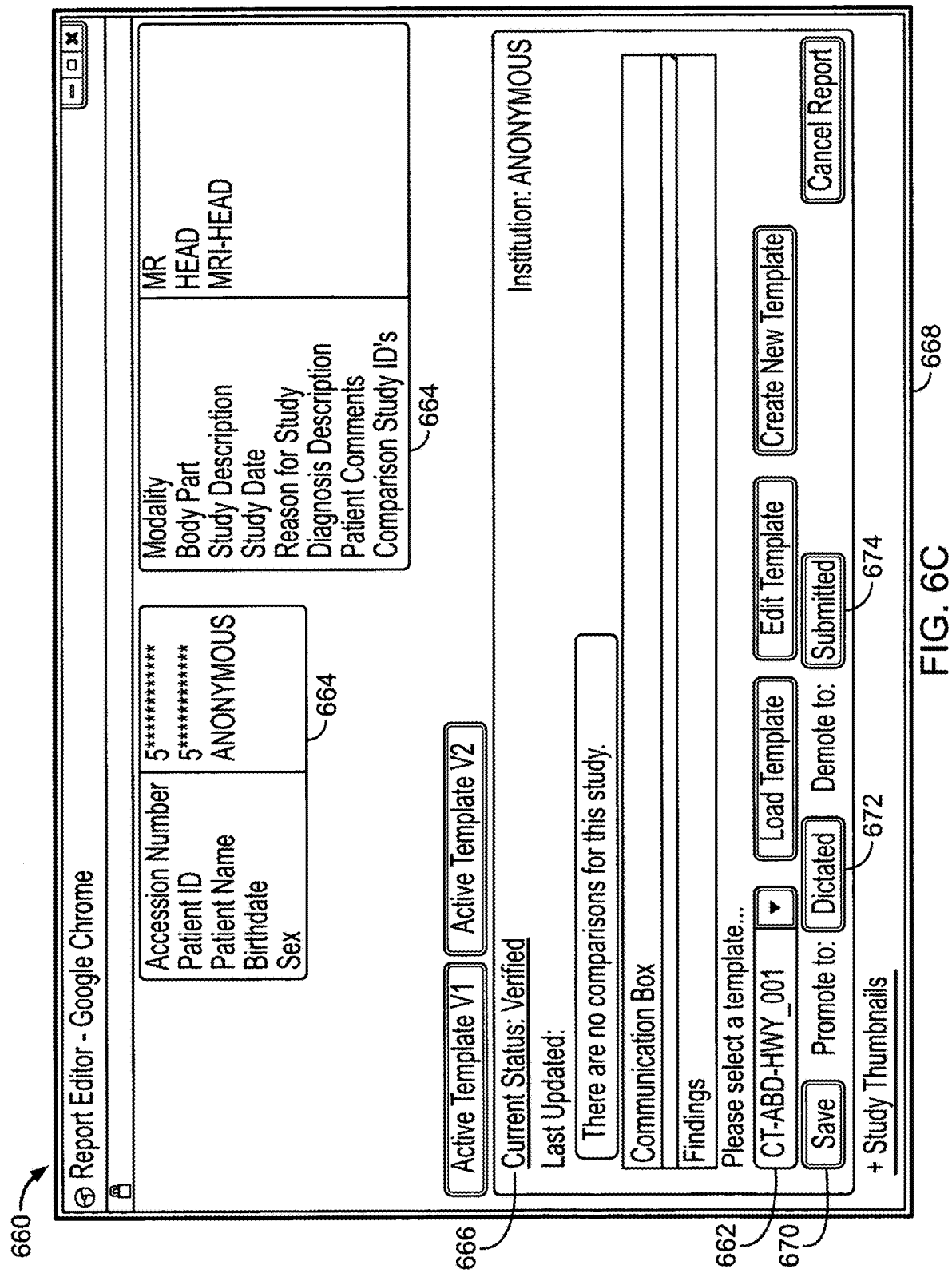
FIG. 6C shows an example of another template selection interface.

In situations the user cannot find a desired template, the user can create a new template by activating a "new" button 622 and enter the content of the new template in a template editor, an example of which is shown in FIG. 6B. In the example template editor 640 displayed in an interface 642, a window 644 is available for a user to enter template contents, e.g., in the form of source code. The user can choose to save (646) the entry, save the entry with a new name (648), create (650) another new entry, or leave the interface 642 back to the selection interface 600 (652). In some implementations, the interface 642 also displays a cheat sheet 654 containing notes, explanations, and examples on how to enter the code properly in the window 644 in order to create a new template. A user can choose to save an incomplete template and work on creating the template at a different time.

Figure 6D:
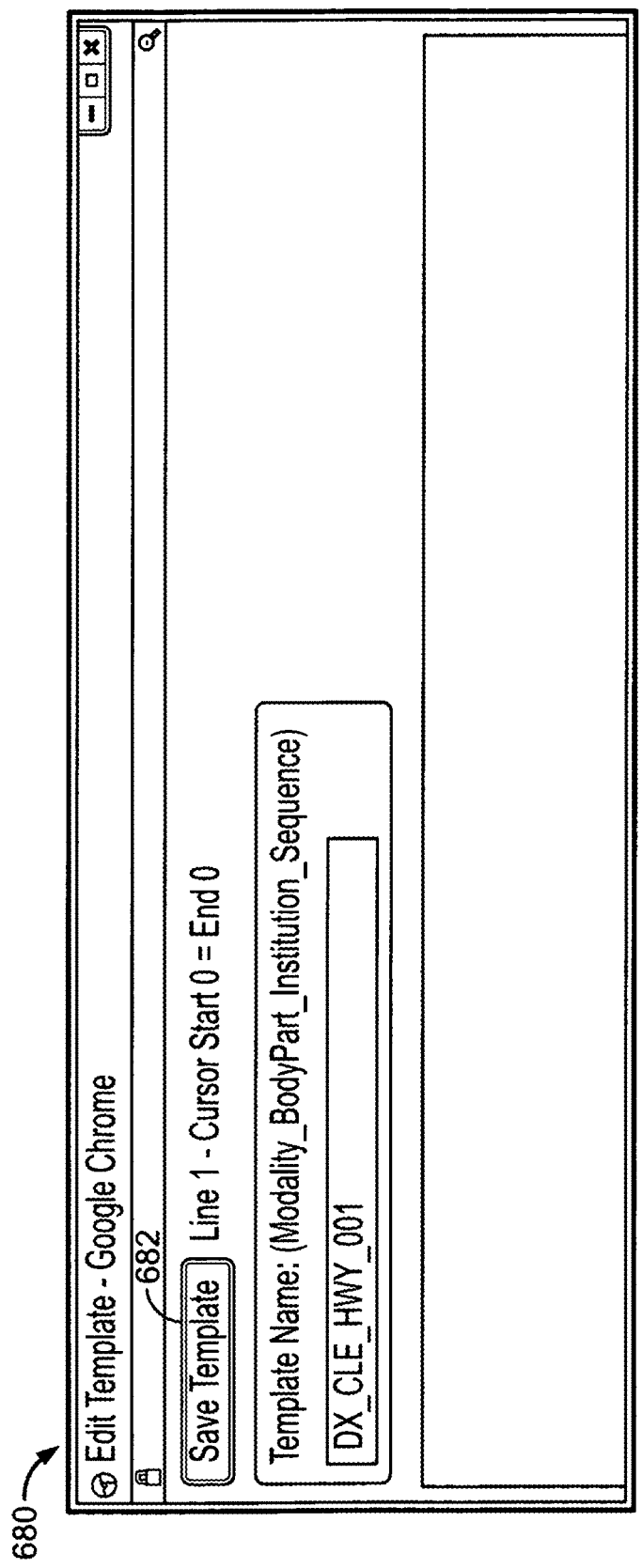
FIG. 6D shows an example of another template editor.

The template editor can also have other forms. An example editor 680 that has a different form than the editor 640 of FIG. 6B is shown in FIG. 6D. Compared to the editor 640, the editor 680 has a "Save Template" button 682. Through the editor 640, an authorized user can name the edited template anything the user would prefer.

Referring again to FIG. 6, when a user chooses to edit an existing template, which can be a complete template or an incomplete template, an interface similar to the interface 642 of FIG. 6B displays another template editor similar to the template editor 640 of FIG. 6B, except that in this other template editor, there is existing entry in the window 644. In some implementations, the different actions, including loading the template, editing the template, and creating a new template, require different authorization levels. Only users having a predetermined level of authorization are allowed to perform a certain action. For example, a user needs to have administrator's authorization to edit or create a template, while any registered user may be able to load and use the template.

The selection interface 600 of FIG. 6 also includes a cheat sheet 660 that provides instructions to a user for using a loaded template in generating a report. Referring to FIG. 5, as an example, a loaded active template 500 for X-ray of the chest performed at institution Healthway version one is displayed on a template interface 502. The active template 500 can be in the text form and can include structured template elements. Each template element includes one or more words or phrases that can describe the study. Some template elements contain alternative descriptions of the study and a user can choose among such descriptions. The template elements can structured into categories including technique 504, comparison 506, clinical history 508, impression 510, patient position 512, mediastinum 514, etc. Each category can be labeled with a header in bold. The header can be chosen to describe the category of template elements. There can be other categories for this study. The categories are chosen such that each category describes the study under one criterion, e.g., medical method, patient information, etc. A cheat sheet 530, e.g., the same as the cheat sheet 660 of FIG. 6, is also displayed in the interface 502 to help a user in choosing the template elements.

The template elements are structured by subject matter experts who are knowledgeable about different areas of studies. Display of the structured template(s), e.g., in the form of categories, can guide a user through a complex classification one step at a time. In addition, both diagrammatic and example based decision support by the decision support system can be provided to the user in synchrony with the template elements contained in the active template(s).

Figure 5A:
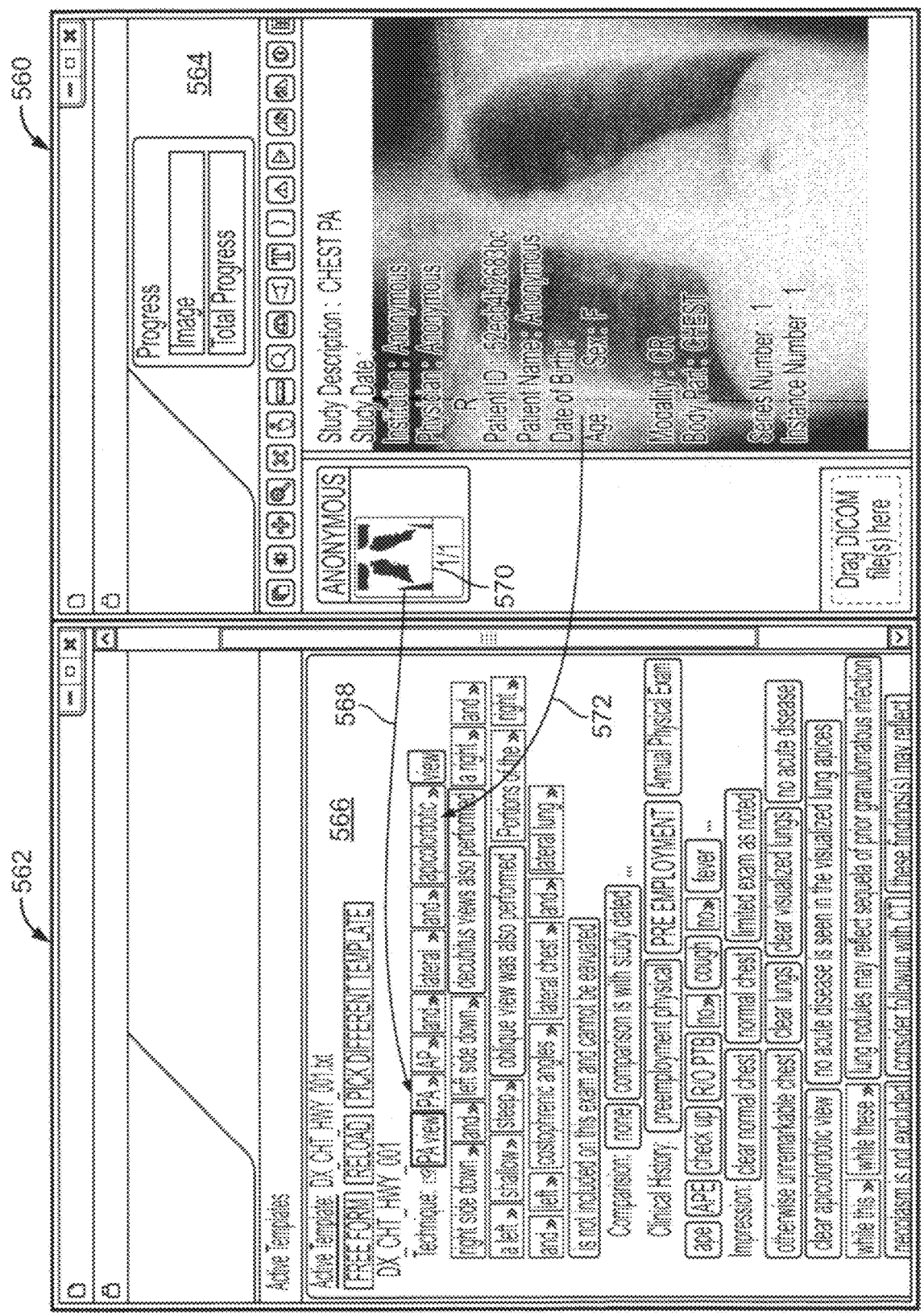
FIG. 5A shows an example of a simultaneous display of a viewer and an active template.
Figure 5B:
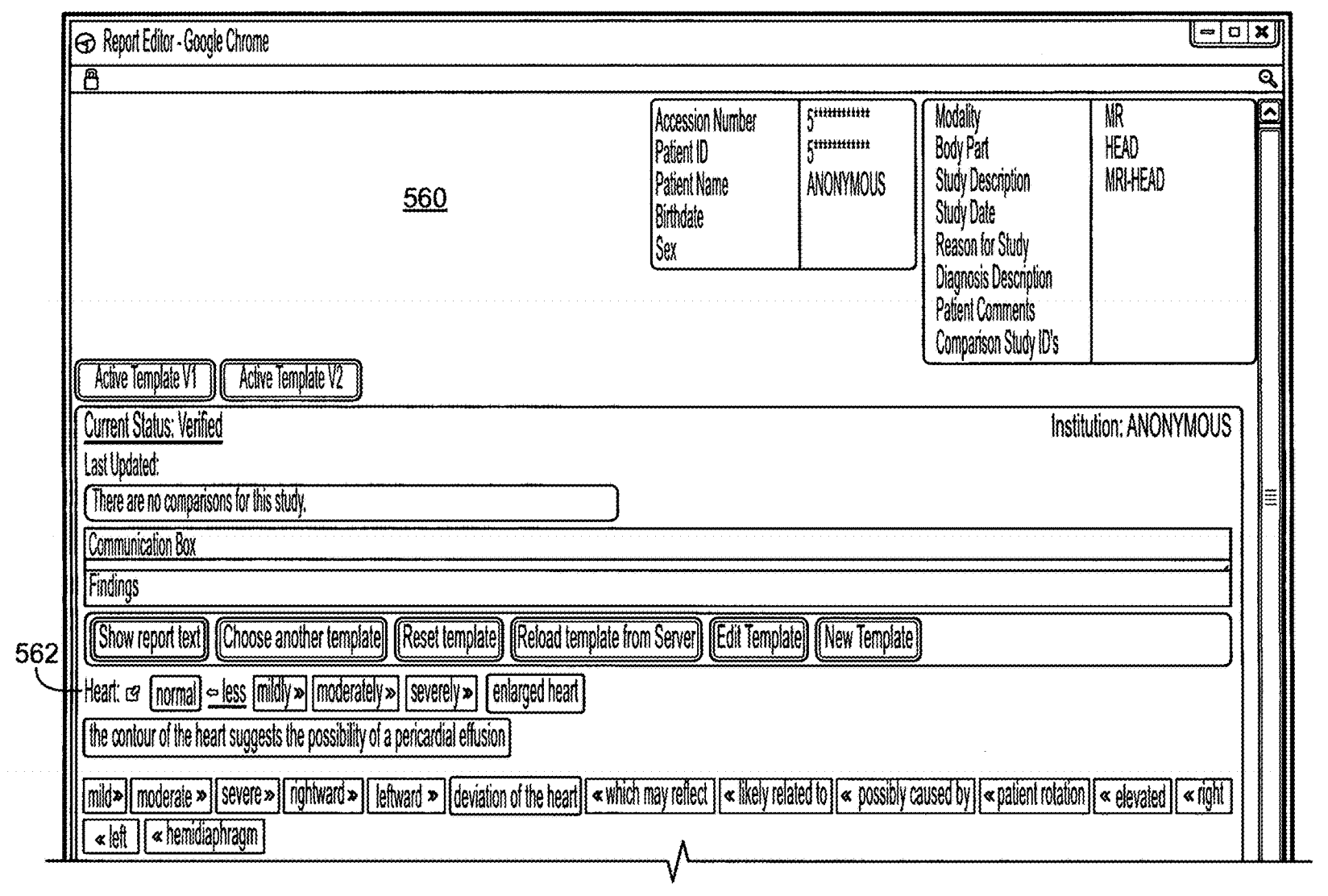

In some implementations, a template is displayed in a so-called guided mode. In this mode, the active template is presented to a user line by line with all built-in template elements, such that a user without substantial experience, e.g., a beginner, can evaluate an image for classification one category or criteria at a time. For example, following display of the template elements, a user first evaluates heart size on a chest X-ray, and then the aortic configuration. In the guided mode, the active template(s) present one structure or finding to be evaluated at a time. The decision support system can similarly present information relevant to correctly classifying the image related to the category or criteria being evaluated. An example of a template 560 displayed in the guided mode is shown in FIG. 5A. In the template 560, only one category 562 "Heart" and its template elements are displayed. Before a user selects the template elements in this category, no other categories are shown.

Alternatively, a template is displayed to a user in a so-called expert mode. In this mode, all categories of the template are shown to the user. The user applies his/her knowledge to build the report by noting what is abnormal or requires comment/editing. Generally, a user using the active template(s) in the expert mode is an experienced user. In the expert mode, the user can view the entire active template all at the same time. Based on the user's experience in classifying similar images on the viewer, the user can jump directly to any point in the active point and select only those template elements relevant to classifying the pathology demonstrated on the image. Any one or more irrelevant categories can simply be ignored. In some implementations, the user can simply note directly that the image is normal and accept the default normal values encoded in the active template. In this expert mode, the user can also move to those areas of the template that need editing and expand the selections to note the abnormalities by mouse selection or touches. Alternatively, the user can also drag and drop the images being studied into the active template to automatically annotate the images based on the location(s) at which the images are dropped into the active template. Drag and drop is described below in more detail.

The template 500 of FIG. 5 is in the expert mode. Another example of a template 570 in the expert mode is shown in FIG. 5B. Compared to the template 500, the template 570 is incorporated in a report window 574, which includes DICOM header information 576, current status 578, and findings 580. From this window 574, a user can access the report generated from the active template 570 and in the text form through a button 582. For the purpose of discussion, the description below focuses on the template 500 of FIG. 5. The description is also applicable to the template 570, unless otherwise specified.

A user of the template 500 can go through the template elements one by one and choose the applicable ones based on his/her study of the record of the patient, e.g., the images shown in a viewer. For example, when the image studied shows a PA (posterior-anterior) view, the user chooses the "PA view" template element 532. Each template element is can be chosen by a mouse click or a touch on the element one or more times or via drag and drop of the appropriate image from the viewer.

A user can determine whether the text of the selected template elements should be displayed in the final text version of the report in both findings and impression, impression only, or findings only. For example, the user can determine by making different number of clicks on the template elements. The template elements may change color to reflect the determination (described further below). In some implementations, the "Findings and Impression" sections in a report relate more to findings being something observable, whereas the "Impressions" sections can convey not only the finding, but also what the finding means related to a diagnosis. In each category of the active template, template elements that describe findings, impression, and both findings and impression are listed for a user to choose. In some implementations, the selected template elements, e.g., for findings and/or impression, are displayed in both sections of the active template, while sometimes findings are reported only in the body of the report and impressions are only in the impression of the report.

In some implementations, the template elements are shown in an initial color, e.g., grey, and each click or touch on the template elements changes the shown color to a different color. As explained in the cheat sheet of 660 of FIG. 6, a template element can turn into three different colors from its original color when the user clicks on or touches the template element for different numbers of times. For example, when a user clicks on an unselected template element once, the template element turns green and becomes selected. This selection will incorporate the content of the template element in both the report and the impression list. The user can click on the selected, green-colored template element again (i.e., two clicks in total) to turn the template element into red. The so-chosen template element is then only included in the impression list, and not in the report. Finally, the user can click on the selected, red-colored template element (i.e., three clicks in total) to turn the template element into blue. The so-chosen template element is only included in the report, and not in the impression list. If the user clicks on the blue-colored template element, the template element returns to the unselected status and becomes gray. Colors other than grey, green, red, and/or blue can be used, each color can correspond to different choices of the template elements, and/or different click numbers can be associated with the different choices.

In some implementations, some of the template elements are associated with each other such that when a user selects one of the template elements, the other associated template elements are automatically selected. For example, some template elements are adjectives or modifiers that are frequently used to describe other template elements that are features of choices for a finding. For example, small round microlobulated are adjectives commonly used to describe a lung nodule. The associated elements can also form an element cluster, e.g., commonly associated findings. Real time guidance can be triggered when one element of an element cluster is activated. Selection of adjectives of a choice can trigger automatic selection of the choice. For example, the template element "AP" (anteroposterior) 534 and the template element "PA" 536 each is associated with the template element "view" 538 so that when either the element 534 or the element 536 is selected, the element 538 is automatically selected. Additionally, selection of some adjective/modifiers can trigger alternate choices. For example, when a user selects a modifier like "multiple," an alternate choice which includes pluralization of the choice is automatically triggered.

In some implementations, some template elements are mutually exclusive or internally inconsistent, such that choosing one precludes choosing the other. For example, cardiomegaly and small heart are mutually exclusive. The active template may automatically gray out a template element that is exclusive to a chosen template element so that the user does not mistakenly choose exclusive/inconsistent template elements.

An active template can also have default selected elements. For example, "PA view" in the technique category 504 or "Normal" in the heart category 520 is a default selection. When a user selects anything in the same category that is different from the default selection, the default selection is automatically deselected. The default selections can help improve a user's efficiency. Also, with the default selections, a complete report can be generated to describe the medical status of the subject in all aspects, without a user needing to choose typically normal features or needing to drop these normal features from the report.

In some implementations, a user may want to describe a study or part of a study, e.g., the technique, using template element(s) that is not listed. The user can create additional template elements at the end of a corresponding category. In the example shown in FIG. 5, a user can click on the dots 540 at the end of a category to open a fillable text box 540. In the alternative template 570, instead of dots 540, the user can click on pencils 572 located at a similar location as the dots 540 in the template 500. The user can then enter desired words or phrases into the text box 540 to form a new template element. The newly formed template element can have the same features as the existing template elements.

In some implementations, for a category, multiple of the same header may be needed to describe or summarize a study. For example, a study may demonstrate multiple lung nodules. Or the user may want to describe the superior mediastinum separately from the middle mediastinum. The template 500 shows only one header 513 for right lung nodules and one header 519 for the mediastinum. However, a user can expand a header under a category by clicking on an expansion sign (or a plus sign) 544 located next to the header. In this example, by clicking on the expansion sign 544 next to the mediastinum header, additional identical headers appear in the template. Multiple clicks can lead to addition of multiple additional headers.

In some implementations, a user may not remember or understand the terms in the template elements, making it hard for the user to make the correct choice. In other implementations, a user may not be experienced in the field of the study, e.g., a medical student or trainee, or a medical professional whose specialty is in a different field. The use can access a decision support system that helps the user understand the terms and/or the field of study. The user can access the decision support system through multiple interfaces, e.g., the interface 402 of FIG. 4 or the interface 502. On the interface 502, signs 548 at different locations, e.g., near category names or within a template element, can be activated via mouse click(s) to access the decision support system. In some implementations, when a sign 548 near a category name is activated, the user is directed to a part of the decision support system associated with the corresponding category; when a sign 548 within a template element is activated, the user is directed to a part of the decision support system associated with the content of that particular template element. In some implementations, a user can perform cognitive matching or classifying of image data using the template elements with the assistance of the decision support system. Details of the support system are described further below.

In some implementations, not all template elements need to be chosen manually by a user. Instead, one or more, or many template elements can be automatically chosen based on a user's interaction with the viewer and/or the decision support system. For example, a user may drag and drop an image from a viewer, e.g., the viewer 400 of FIG. 4, onto a category of the template, the correct template elements are automatically chosen without needing the user to analyze the image or manually make the choice. An example of the drag and drop process is shown in FIG. 5A, where a viewer interface 560 and an active template interface 562 are simultaneously displayed to a user for an X-ray study of a patient's chest. The viewer interface 560 shows a viewer 564 that has similar or the same features as the viewer 400 discussed with respect to FIG. 4. The template interface 562 shows an active template 566 that has similar or the same features as the active template 500 of FIG. 5. A user can drag and drop (568) an image 570 in the thumbnail format from the viewer 564 onto the technique category, e.g., on any of the selectable template element, the template elements "PA" and "view" automatically selected because the system 100 automatically determines the view of the image 570. Alternatively, a user may also drag and drop (572) the image in the working region of the viewer using the drag and drop tool in the tool set.

When a user uses drag and drop of a PA chest image to select the "PA" template element, the system 100 obtains information about the image, which allows for the automatic selection of the template element. The information includes that the image represents a specific view of the chest, i.e., a PA view and that the image is identified as a PA view for the purposes of examples for beginners as to what PA views look like. As a user reviews the case, additional information about the image is obtained, e.g., when the user identifies that there is cardiomegaly. The additional information is added, e.g., concatenated, to the existing information about the image known by the system 100. As a result, the system 100 can now automatically identify a PA chest which demonstrates cardiomegaly.

In addition, when a user selects a modifier using drag and drop, the choice associated with the modifier is automatically selected. In some implementations, when a user drags and drops an example of complex pathology, which has a common best practices description from the decision support system, the active template is automatically populated with the best practices with some of the elements "pre-selected" or automatically selected. Choice of some active template elements may trigger pre-selection or addition of template elements based on the attributes of the selected active template elements. For example, selecting a type I, II, III, IV, or V Rowe classification calcaneus fracture would automatically add appropriate best practices descriptions and potentially automatically preselect the modifiers and choices as appropriate to describe that type fracture.

When a template element is selected, e.g., manually or automatically through drag and drop, attributes, which are data or functions that have previously been assigned to the selected template element, are triggered. Each template element (in the form of an object) can have unlimited attributes. The tool objects of the viewer and objects in the decision support system can have similar features. The attributes can be data attributes, e.g., numerical, alphabetical, or both, which can be fixed or variable, or function attributes, e.g., functions that cause a tool in the viewer to be displayed and highlighted, or that cause an SMS to be sent. Examples of data attributes include ICD-9/10 codes associated with the template element within the active template(s). For example, if a "Cholecystitis" related diagnosis is chosen in an active template, the ICD-9/10 code would automatically be assigned to the corresponding image(s)/record. Examples of function attributes include presenting the Boehler's angle measurement tool in the viewer when a user selects a template element in the corresponding active template noting a calcaneus fracture. Another example of a function attribute is associated with the function of inserting into an active template diagram by drag and drop. For example, an acromioclavicular separation Type II image can be dragged and dropped into an active template at the AC (acromioclavicular) joint element, which then can trigger the auto-annotation noting a Type II AC separation onto the image, and measurement tools to measure the AC separation distance can pop up in the viewer displaying the image.

Each data attribute has a value, e.g., a number, and a unit associated with the value. The value and the unit can be encoded in their corresponding template element. When a template element is chosen, the system 100 automatically associates the corresponding attribute value with the image/study or user, and places the attribute value into a database, e.g., the database 114 of FIG. 1, and on the image being studied, if appropriate. In some implementations, a subject matter expert determines at the time of adding the attribute whether it is appropriate to place the value into the image, database, or both. Examples of values include ICD-9/10 codes related to imaging findings and measurements, which can be inserted into the report and/or be auto-annotated onto the image and user mistake scoring. User mistake scoring is discussed further below.

Figure 5C:
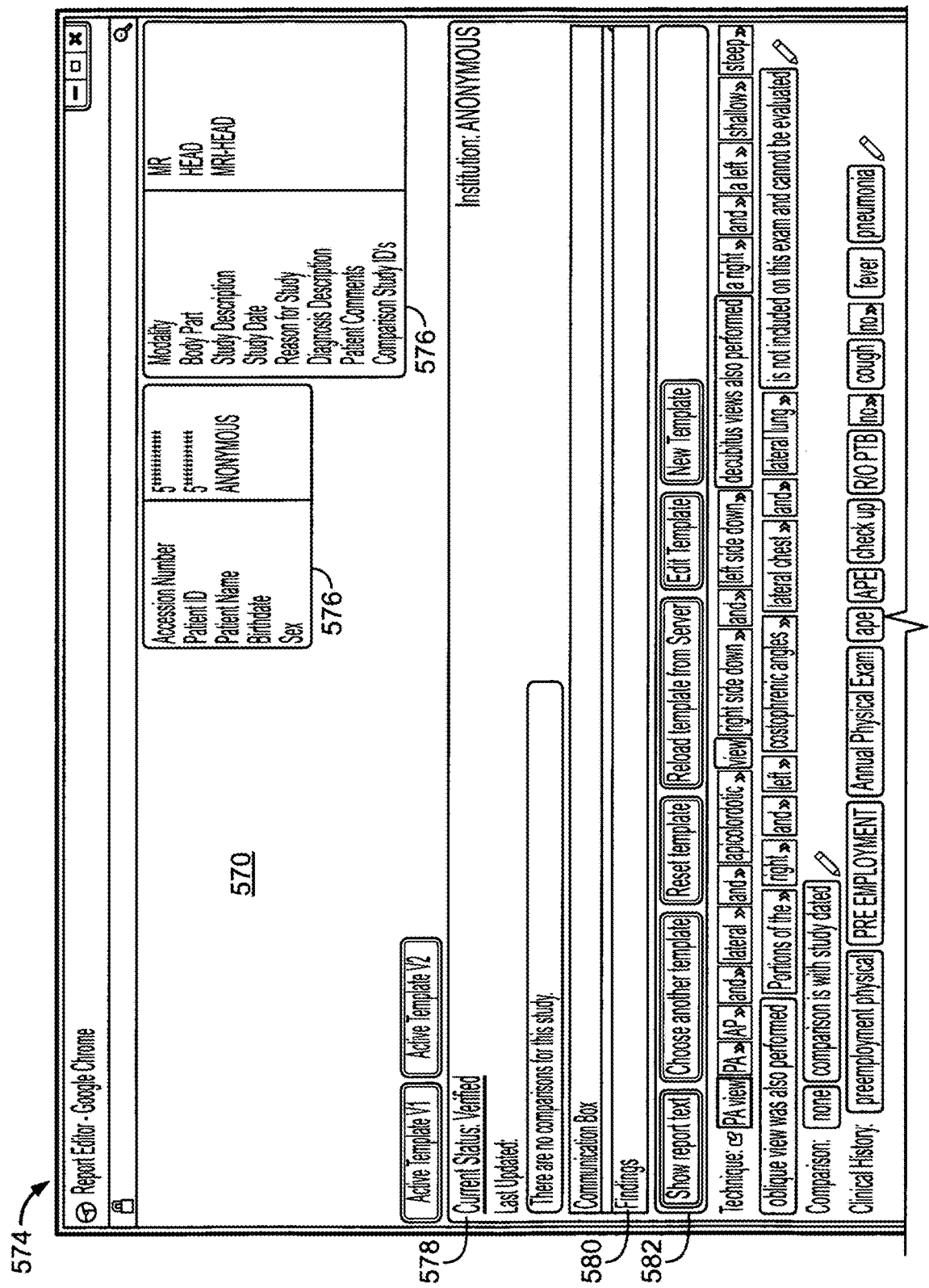
FIG. 5C shows an example of another active template.

In some implementations, not all template elements in a category are directly shown in the interface 502. Instead, the template elements can be nested, e.g., under a "more" button 546, to keep the template short and neat in its presentation. Sometimes an experienced user, e.g., a medical professional trained in the field of the study, may not need to review all possible template choices and can make a diagnosis quickly by directly entering his/her diagnosis/comments in each category or in selected categories. The nested template elements can expedite the experienced user's diagnosis process. Sometimes in a category, the most frequently chosen template elements are directly displayed while the other template elements are nested. Other times all elements in a category are nested. When all elements of all categories of a template are nested, the template is in a collapsed mode. The template 570 of FIG. 5C is in a collapsed mode.

For the template 500 of FIG. 5 to be in a collapsed mode, instead of only the categories 518, 520 in FIG. 5, all categories of a template are displayed in the collapsed manner. Without expanding the categories to display the template elements, the user may directly enter "normal" or "abnormal" within each category or selected categories that are necessary for the diagnosis, e.g., in the category 520.

In some implementations, through the guidance of the system 100, e.g., links on various interfaces, a user of the expert mode can also gain access to diagrams and/or examples of normal and abnormal findings recorded in a decision support system. The user can choose a relevant match in either a diagram or an example. Based on the user's choice, the system 100 can update the active template with the relevant template elements that describe the image findings, annotate the image, and/or append the auto annotated image to the report.

The system 100 can automatically evaluate the consistency between the measurements made in the viewer and the finding/pathology made in the active template. For example, if user measures the AC distance to be 4 mm and selects an active template element that says there is an AC separation, then the system 100 can warn the user, e.g., through a popup, that the measurement and the selected active template element are in consistent. On the other hand, if the user measures the AC distance to be larger than 6 mm and chooses presence of AC separation, or measures the AC distance to be smaller than 6 mm and chooses absence of AC separation, the system 100 would not warn the user of any discrepancy between the distance measurement and the choice of active template element. Typically, the measurement ranges associated with different template element choices are defined by subject matter experts.

Reports generated using the active template(s) can have standardized formats and can make communications, e.g., among different entities or individuals, easy. A user can leverage the information provided automatically by the viewer, such as the viewer 400 of FIG. 4, and the decision support system to generate a report. A user can generate or access a report associated with an active template directly from the active template. In the example of the template 500 of FIG. 5, a user can activate the report button 505. In the example of the template 570, a user can activate the show report text button 582.

A report stored in the system 100 can have different statuses, including a new status in which a report is not generated or completed; a submitted status, in which the report is completed by an initial reviewer; a verified status in which the report is reviewed in a standard radiology report format, or text format; a dictated status advanced from the verified status, in which the report is noted in the system 100 as being ready for review by a second, advanced reader for quality assurance; a preliminary status in which the report is updated by the quality assurance reader; and a final status, in which the report is ready for delivery to a client. The report statuses can be altered in both the advancing direction and the backward direction. As an example, the initial reviewer can be a beginner and the generated report can be in the verified status. The initial reviewer can then choose to advance the verified report to a dictated status to notify the system 100 that the report is ready for review by a second, advanced reader for quality assurance. The advanced reader then changes the status of the report into preliminary. Revision of the standard text version of the report can be toggled back to the template version effortlessly so that a second reader can review the exact choices made by the initial reader and easily modify the report potentially by a combination of de-selection of choices and modifiers as well as selection of previously unselected choices and modifiers. Similarly, revision of the template version of the report can automatically revise the text version of the report. The status of each report for each case is listed in the worklist 300 of FIG. 3, as status 330.

A report can be displayed in different forms on a user interface to a user. The forms can include the active template form which includes color-coded user selections of active template elements, a text format which includes a non-editable text output of the active template with the user selections, and a free text format. The template form and the text format are generally independent of the status of a report. In some implementations, the free text format is available only in the preliminary status. In the free text format, a user is allowed to perform additional review and to edit the report. A report in each different status can be shown in multiple different formats. For example, when a report is in the verified, the dictated or the preliminary status, the report can be toggled between the active template format and the non-editable text output display. In some implementations, a report in the final status is non-editable and shown in the text format.

Figure 8A:
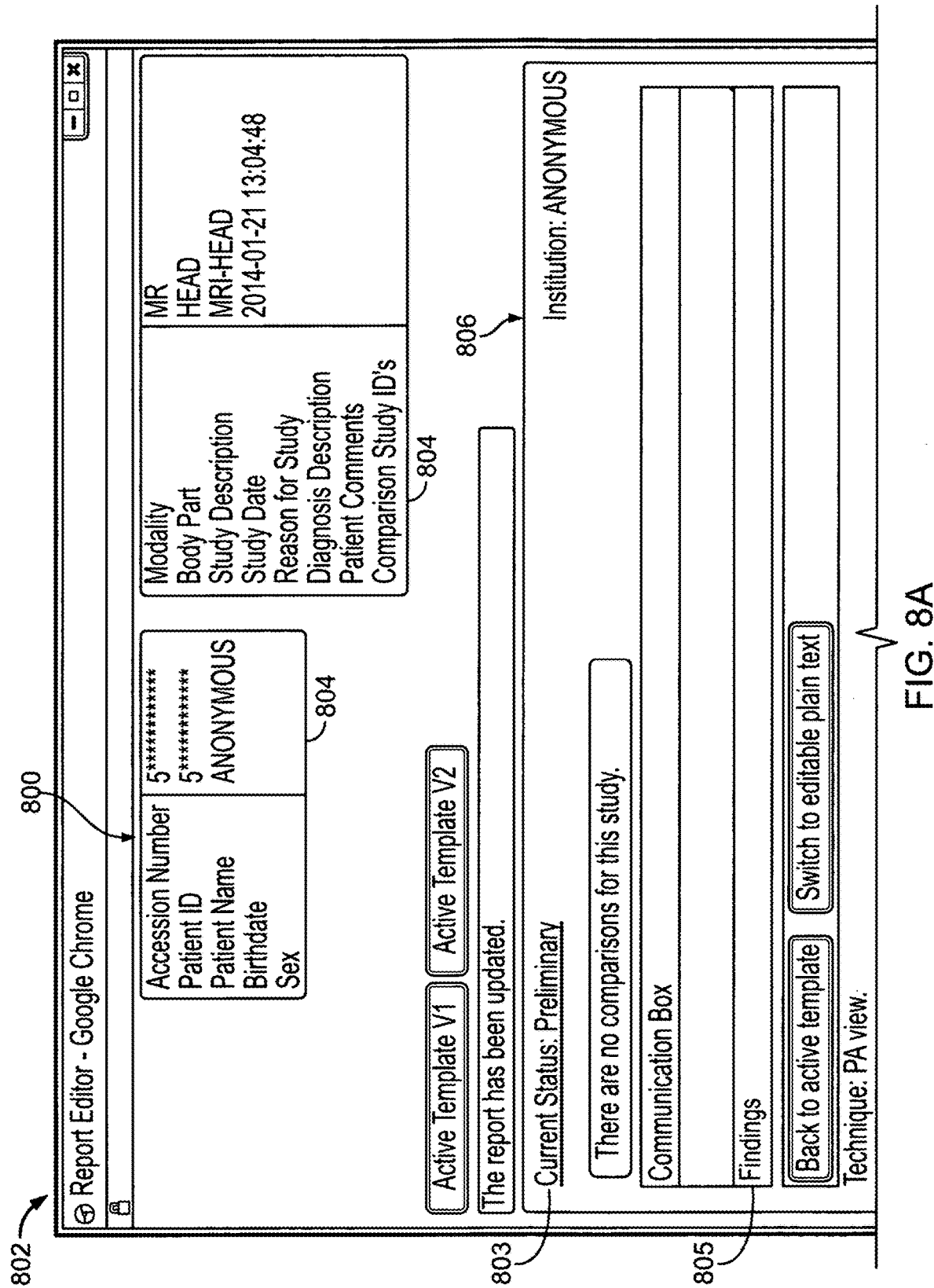
FIG. 8A shows an example of a preliminary report.

An example of a preliminary report 800 is shown in FIG. 8A. The report 800 can be viewed in an interface 802 and can contain patient information 804, e.g., in the form of a DICOM header. The report 800 also contains report information 806, which includes the current status 803 of the report and findings 805 in text. A user can save or change the current status 803 of the report using buttons 807. The report 800 can also contain study thumbnails 808, the expansion of which shows one or more images of the patient for whom the report is generated. As described previously, a user can drag and drop the image(s) into the report. An authorized user, e.g., a user with a desired level of experience, can verify the report, e.g., by reviewing choices made in the associated template(s). The authorized user can be the user who generated and submitted the report, or a different user when the user generated and submitted the report is a trainee.

Figure 8B:
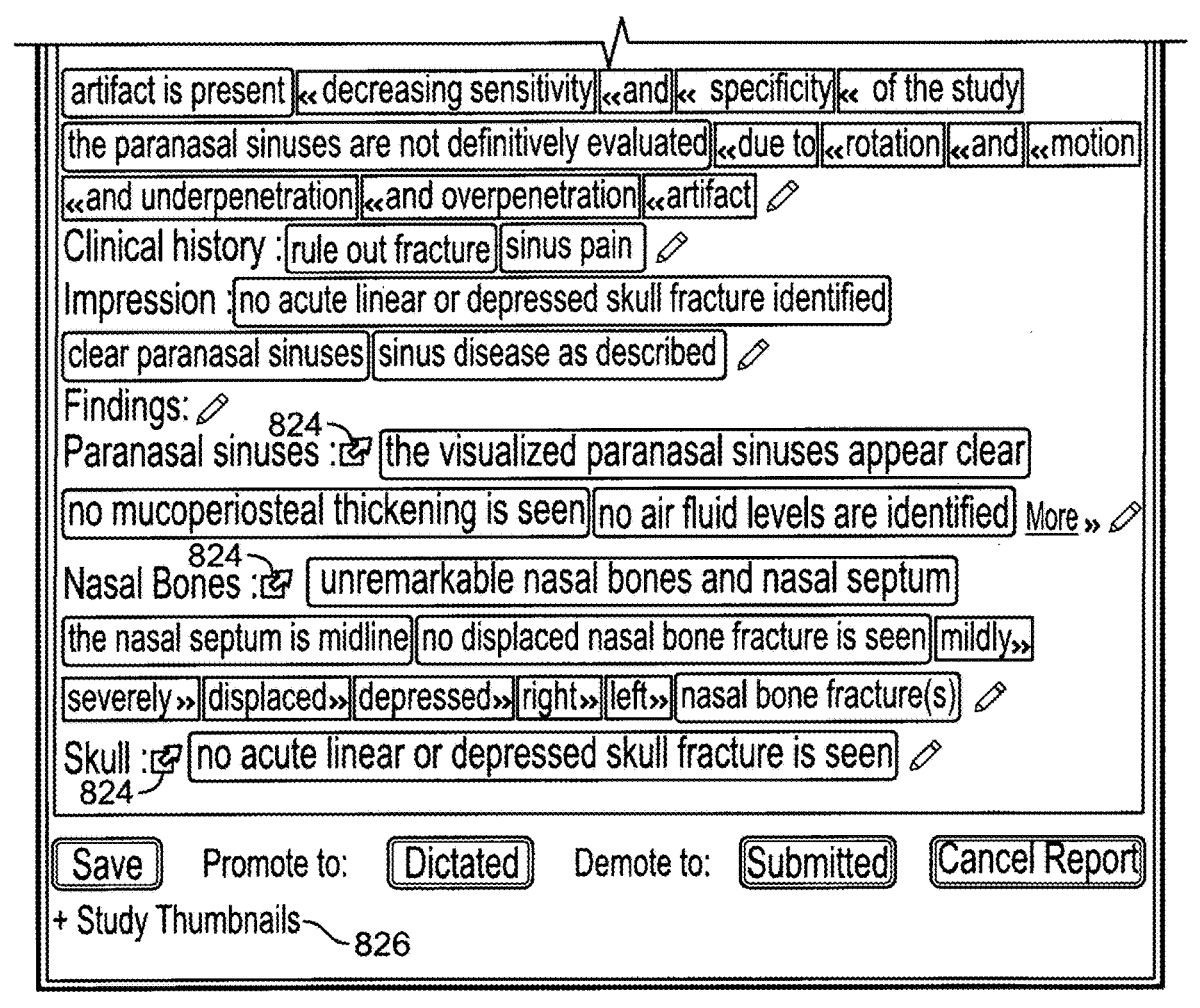

FIG. 8B shows an example of a report 810 in the verified status in the template mode displayed in an interface 812. The report 810 contains patient information 814 and report information 816, both of which being in the form of a DICOM header and similar to those contained in a submitted report. The report 810 also contains findings 818 of the study or diagnosis. However, instead of being in text, the findings 818 contain selected template elements from a corresponding active template. The findings 818 contain all categories of the active template that are relevant to the study and the chosen template elements. In some implementations, some findings are critical findings, i.e., time sensitive in patient care, and the system 100 can send auto notifications of such critical findings to the patient's primary medical doctor, hospital, RN (registered nurse), or the patient himself/herself. Similar to those categories and template elements in a template, the categories and template elements in the verified report can be edited, new categories and template elements can be added, some template elements can be nested. In addition, a user can access the template selection interface or the decision support system interface through the report 810, e.g., by activating buttons 820, 822, 824. The verified report 810 also contains the same study thumbnails 826 as its corresponding submitted report.

In some implementations, when the active template is incorporated in a report window, e.g., the report window 574 of FIG. 5C, the active template displays all selected template elements. For the purpose of discussion, the report 810 is used as an example. The descriptions are similarly applicable to the report of FIG. 5C.

The report 810 additionally includes a communication box 830 which is found in all statuses of the report and can be used by anyone involved in the acquisition through report review and beyond to communicate with anyone involved in the imaging chain/life cycle of the study report. For example, it can contain communications from a client technologist noting patient history or issues related to the ability to do a quality study such as patient motion, or immobility through to feedback from a surgeon, a lab, a clinician, or a patient which can be used to notify the system of independent information related to the diagnosis/diagnoses suggested by the Final report. The feedback can include opinions such as agree or disagree, and/or data entry if specific surgical, laboratory, pathology correlation is performed.

In some implementations, the active template(s) logs all choices a user makes and the system 100 can provide feedback to the users on an individual basis using the logged choices. For example, the discrepancies between choices made by a less experienced user and those made by a more experienced user can be recorded and provided to the less experienced user. The less experienced user can learn through this process and improve his/her skills.

In some implementations the sequence of user choices can be shown in a playback mode so that a beginner user or an advanced user can evaluate the process as performed by the other. In addition the time spent on each choice can be identified to determine the time spent on each Header/Category. The identified time can be used to help identify areas of improvement.

In some implementations, the system 100 can provide real time feedback on accuracy of user choices or diagnosis directly in the active template. The feedback can be triggered when the user has reached a predetermined miss rate threshold. For example, a user who keeps missing renal cysts would start to see the color of the "renal cyst" template element in the active template turn yellow as a caution indication. The user is alerted to specifically evaluate the choice. Sometimes the user can even be required to choose positively or negatively whether a specific finding is present or absent before submitting a report based on exceeding a threshold. In another example, real-time feedback can include pop-ups of the miss rate threshold and its related warnings and guidance.

In some implementations, the system 100 is used in a dual read, teaching, or learning mode, in which feedback is provided to a beginner or a learner automatically by the system 100 and/or by a more experienced user. Some features related to the dual read or feedback have been discussed previously. In addition, a user's diagnosis process or report can be examined and evaluated by another user, e.g., a more experienced user or a quality assurance user, or the system 100. The examination can be performed in resident training of the user. The system 100 may allow the more experienced user or quality assurance user to study the record of the patient based on which a trainee made his/her diagnosis or report. The experienced user can change the existing diagnosis or report of a less experienced user through the active template(s). The less experienced user can be evaluated based on the differences between the choices made by the two users in the active template(s). The system 100 can then generate a mistake score for the trainee to reflect a discrepancy between the trainee's diagnosis or report and that of the more experienced user.

In some implementations, the more experienced user or quality assurance user can score a trainee's diagnosis process or report by reviewing the stored viewer, template(s), and report(s) based on which the trainee made his/her diagnosis or report. In some implementations, the system 100 allows a user to use the system in a playback mode, in which the user can play back the time and sequence of each mouse click. For each trainee, the system 100 can automatically accrue a lesion conspicuity score and clinical severity score when a more experienced user uncovers a miss in the diagnosis or the report, without the more experienced user doing any additional work. For example, the findings or template elements of an active template, e.g., the active template 574 of FIG. 5C, can also contain attributes such as "Severity" and "Conspicuity". The values of these attributes can be automatically set by the system 100 when a subject matter expert modifies a beginner's choices. The system 100 can generate a grade for the beginner as a byproduct of a more experienced user correcting the report choices.

The scores/grades for users can be shown using features of the RIS (Radiology Information System). For example, field filter function can be applied on a worklist for a specific trainee. Depending on the specific question used in the filtering, an overall score for the trainee or a specific score based on evaluations on a specific modality body part can be retrieved. The system 100 can also rank the trainees. For example, the system 100 can automatically correlate a trainee's rank number, e.g., compared to either norms or a cohort, with severity of misses, his/her conspicuity score, and the user efficiency related time stamps, i.e., time spent on a study. The system 100 can also automatically score the users based on the correlations to reflect the users' efficiency and accuracy in classifying normal and abnormal findings. Conspicuity scores associated with certain pathology may depend on the features of the pathology. For example, when the pathology is a lesion, the conspicuity score is related to the size of the lesion and the conspicuity attribute can have a size range associated with a specific conspicuity score.

In some implementations, choices made in the active template(s) and images dragged into the active template(s) populate the decision support system with examples. For example, the system 100 can enable the user to identify through the interface(s) displaying the template(s) and/or the decision support system, one or more choices or images as representing an example for the decision support system in an appropriate study. One or more moderators can verify whether the examples are appropriately and correctly listed in the decision support system. In some implementations, a user's drag and drop action triggers a moderator's review.

Decision Support System

Figure 7:
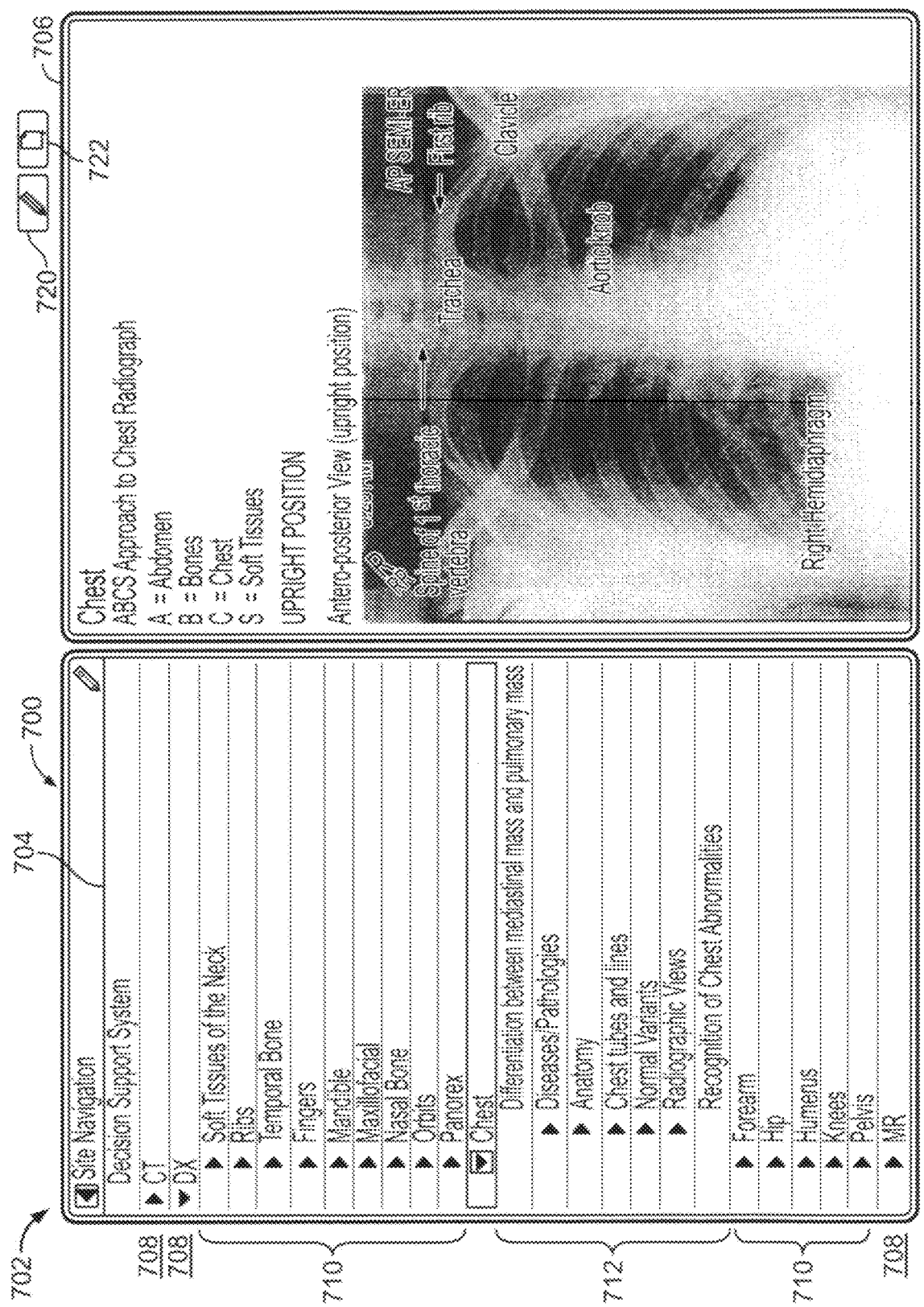
FIG. 7 shows an example of a decision support system.

As described previously, a user can access a decision support system through other interfaces, e.g., a viewer interface or an active template interface. An example decision support system 700 is shown in FIG. 7. A decision support system interface 702 displays the support system 700 to a user. The decision support system 700 can aid the user with relevant' information and content for generating a report based on information from the viewer and from the active template. The system 700 can leverage information which is already known in the field as a byproduct of the users' viewing the images and interacting with the active template(s) so that relevant content of the information is provided to the user at the time and point of contact with the user.

Similar to the template elements that have attributes, the decision support system also contains elements that support data attributes, which can be static or variable, and function attributes. In some implementations, the elements in the decision support system can be tagged with unlimited attributes. The tagging can be related to context sensitive presentations of the elements to the user, and/or the behavior of the attributes, e.g., when the elements are dragged into a report or clicked on to produce changes in either the active template(s) or the viewer.

Example elements in the decision support system include images, diagrams, and texts. For example, in a part of the decision support system related to calcaneus classification, actual examples of calcaneus fractures with text elements noting key features of the various fracture types are provided. Each of the elements, which can be X-ray images, diagrams, descriptive texts, and others, can activate active template functions, including inserting additional template elements into an active template for use in describing the calcaneus fractures illustrated in the elements. Some attributes ascribed to the elements, including calcaneus diagrams, images, and texts, can activate or trigger specific viewer tools, e.g., the Boehler's angle measurement tool.

In the example shown in FIG. 7, the decision support system 700 is initially displayed to a user in the form of an index in a window 704 that shows a navigation panel. Support elements are hidden under the index and can be accessed when the user reaches the lowest level of the index. When the support elements contain data support attributes, the data can be displayed in another window 706. For example, the support elements contain examples of normal, abnormal, and normal variants, which can be shown in the window 706. In addition, the support elements perform the function of informing active templates of relevant "choice/modifier template elements, and/or informing the viewer which tool(s) to use and how to use it.

In some implementations, the index is arranged similarly to the template names shown in FIG. 6A. The highest level 708 of the index sorts the support elements based the medical methods used in obtaining the medical records or images. For example, "CT" represents CT scan, "DX" represents Diagnostic X-ray, "MR" represents MRI scan. The next level 710 of the index sorts the support elements based on the body parts on which the medical methods are applied. The next level 712 further sorts the support elements based on various parameters associated with the medical methods applied to the body part. If necessary, additional levels are added to sort the support elements. In some implementations, multiple user interfaces of the system 100 are displayed simultaneously to a user. To free up display space, e.g., desktop space, the navigation panel shown in the window 704 can be closed or collapsed in its default state.

The correspondence between the template names and the index arrangement can help a user quickly familiarize himself/herself with the system 100 and readily locate the support information needed from the support system 700. In some implementations, the system 100 links one or more template elements of an active template with one or more support elements of the support system 700, such that when a user opens a decision support system from a link nearby a linked template element, the system 100 directly displays to the user the linked support elements. In some implementations, instead of displaying the linked support elements, the index level 710 or lower associated with the body part studied in the active template is displayed. In the example shown in FIG. 7, when a user studying chest results of a patient and accesses the decision support system 700, the index level 712 corresponding to the chest is displayed to the user.

A user can navigate through the decision support system 700 using the index. In some implementations, a user's choices made in an active template can be automatically populated to the support system 700 such that corresponding support information is automatically displayed, simultaneously to the user's actions on the active template.

In some implementations, the decision support system provides different access permissions to different users. For example, all users who are using the decision support system for classifying can access the full system. The support system 700 can be presented to the user in a guided mode or an expert mode, similar to the guided mode or the expert mode of the template described previously. In the guided mode, the category/Header which a user, e.g., a learner, beginner, or trainee, is reviewing in the active template has an automatic link to a relevant page in the decision support system. The link can be predetermined by a subject matter expert when building the active template. In the guided mode, the decision support system follows the user's activity on a corresponding active template in a step by step manner, presenting diagrams, discussions, and examples of normal, abnormal, and normal variant information in the window 706. In the expert mode, the decision support system follows the user based on the user's clicking of the choice and modifier template elements. Experienced users, e.g., experts, can navigate through the decision support system by activating specific decision support system link icon(s) at their discretion.

An authorized user of the support system 800 can edit the contents of the support system through an edit button 720 in the interface 702. In addition, the authorized user may also create one or more new support elements under proper index level to include knowledge that is not currently stored in the system 800. In this example, the user can create such new elements through a new button 722 on the interface 702.

The decision support system 700 can also include example case pages which contain thumbnail images demonstrating common pathologic presentations and descriptions of the images by one or more subject matter experts. The images can help a user in diagnosing, and the descriptions can be used by the user in the report so that the user can be efficient and the report can be standardized. For example, in tuberculosis chest x-ray reports, there are common and characteristic presentations based on stage/severity/chronicity and the descriptions can be done by a subject matter expert and incorporated into the example images on the decision support system as attributes. When an example image is dragged into the active template at the appropriate spot, the attributes are inserted into the active template as new template elements. All reports on the same diagnosis can use the descriptions consistently.

In some implementations, based on the support elements, examples, and discussion information of the decision support system, a user can customize, edit, or make new active templates. For example, additional template elements can be added or some template elements can be modified, based on pre-classified findings recorded in the support system. In addition, known image findings can be incorporated into the support system 700, e.g., an image showing a particular diagnosis can be dragged and dropped into the window 706 that corresponds to the support element for the diagnosis. An expert or administrator authorized in the support system can add additional description or comments to the newly added image findings, including the texts used in the active template elements that describe the findings as attribute of an element of the newly dragged and dropped image in the decision support system. The communication between the template, the viewer, and the decision support system can promote best practices for the classification and its potential variability.

Object Oriented Programming

In some implementations, one or more of the tools in viewers, the template elements in active templates, the elements in the decision support system, including diagrams, images, text blocks, etc., are encoded in a method similar to object oriented computer program code. The attributes of these tools or elements are not limited and can include those initially not contemplated and later added. The attributes are expressed as attributes of objects, where the previously discussed elements in the decision support system, active templates, and viewers can be the analog to objects in computer coding.

In some implementations, values of the attributes initially set in the system 100 may be changed during the use of the system 100. For example, the norms or normal ranges encoded in the system 100 can be adjusted based on actual data generated from use of the system 100. Image data and its corresponding findings can be aggregated for generating more accurate normal ranges. In the example of AC distance, instead of smaller than 6 mm being normal as set initially by a subject matter expert, the aggregated data may show that the normal range may be less than 5.43 mm. Values of these attributes can also be changed in response to actions by a user in using one or more of the interfaces.

In some implementations, the objects (or elements) of the decision support system, active templates, and/or the viewers, can have attributes that are internet links to content external to the system 100. The content can include peer reviewed journals or book chapters that support the use of specific values for the determination of the state of a subject. Elements in the active templates, the decision support system, and the viewer can also link to other pages. For example, within a page of a decision support system, there can be internal links to other pages of the same system. In another example, using icons similar to the link 548 of FIG. 5, a user can link from an active template to the decision support system. Sometimes activation of an element of the system 100 can automatically cause navigation to a specific decision support page.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable digital processor, a digital computer, or multiple digital processors or computers. The apparatus can also be or further include special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit). For a system of one or more computers to be "configured to" perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Control of the various systems described in this specification, or portions of them, can be implemented in a computer program product that includes instructions that are stored on one or more non-transitory machine-readable storage media, and that are executable on one or more processing devices. The systems described in this specification, or portions of them, can be implemented as an apparatus, method, or electronic system that may include one or more processing devices and memory to store executable instructions to perform the operations described in this specification.

While this specification contains many specific implementation details, these should not be construed as limitations on the scope of any claims or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A computer based method comprising displaying simultaneously to a user in a display:
    (a) an image of a subject, (b) information about how to express a determination about a state of the subject based on the image of the subject, the information including a representative figure that corresponds to the image of the subject and is associated with predefined words that at least partially describe the state of the subject, and (c) one or more invocable elements for the user to invoke, each of the one or more invocable elements including a single word or a phrase of two or more words representing at least a portion of the determination about the state of the subject, in response to a selection of a particular one of the one or more invocable elements using a first dragging and dropping of the image of the subject onto the particular one of the one or more invocable elements, displaying additional text based on an attribute of the selected particular invocable element, and automatically displaying a tool based on the selected particular invocable element, the tool usable to make a measurement on the image of the subject, the measurement relevant to the attribute of the selected particular invocable element, storing an association between the image of the subject and a numerical result of the measurement, and subsequent to storing the association, in response to a second dragging and dropping by the user of the image of the subject from a second interface onto a first interface that is displayed simultaneously to the second interface in which the image of the subject is displayed, adding the numerical result of the measurement to a structured report expressing the determination about the state of the subject.

2. The method of claim 1 in which the information comprises at least one normal or abnormal example or diagram.

3. The method of claim 1 in which the one or more invocable elements guide the user in determining the state of the subject by representing possible attributes of the state of the subject to the user.

4. The method of claim 1 in which the information comprises information about relationships between states of other subjects and attributes of other subjects including at least one diagram and at least one example.

5. The method of claim 1 further comprising in response to the first dragging and dropping, automatically annotating the image with the attribute of the selected particular invocable element.

6. The method of claim 1 in which the one or more invocable elements include one or more links to decision support information associated with the attribute of the selected particular invocable element.

7. The method of claim 1 in which the information comprises diagrams or examples.

8. The method of claim 1 in which the user is a first user, and comprising enabling a second user to interact with the one or more invocable elements to change interactions of the first user, and evaluating differences between the interactions of the first user and the second user as an evaluation of a skill of one of the first user or the second user.

9. The method of claim 1 in which the one or more invocable elements represent information provided by a subject matter expert based on the determination about the state of the subject included in the structured report.

10. The method of claim 1 further comprising: sending an automatic notification to a party for action upon the determination about the state of the subject that is indicative of a critical finding that requires time sensitive action.

11. The method of claim 1 further comprising communicating the determination about the state of the subject to a party who has knowledge of an actual state of the subject, enabling the party to report information related to the actual state of the subject, and storing the information reported by the party for use in correlating the determination of the state of the subject included in the structured report and the information related to the actual state of the subject.

12. The method of claim 1 further comprising altering at least one of the one or more invocable elements to indicate to a particular user an aspect of the determination about the state of the subject that requires attention by that particular user.

13. The method of claim 1 in which one or more of the one or more invocable elements are associated with a right side or a left side of the subject.

14. The method of claim 1, in which the one or more invocable elements are divided into two or more categories, and
    in which, in a mode for lower-skill users, the display does not simultaneously include invocable elements of more than one category.

15. The method of claim 1, in which the one or more invocable elements are divided into two or more categories, and in which, in a mode for higher-skill users, invocable elements of two or more categories are displayed simultaneously, and in which the user may choose to invoke invocable elements in only a particular category relevant to a pathology demonstrated on the image of the subject.

16. The method of claim 1, in which, in a mode for higher-skill users, the one or more invocable elements comprise default values that express the determination about the state of the subject without requiring an invocation by the user of the one or more invocable elements.

17. The method of claim 1, further comprising, in a mode for lower- skill users, displaying supporting information relevant to classifying the image of the user.

18. The method of claim 1, further comprising determining that the numerical result is different from a normal value or normal value range associated with the tool, and alerting the user that of the numerical result is different from the normal value or the normal value range associated with the tool.

19. A computer based method comprising displaying simultaneously to a user in a display:

(a) an image of a subject, (b) information about how to express a determination about a state of the subject based on the image of the subject, the information including a representative figure that corresponds to the image of the subject and is associated with predefined words that at least partially describe the state of the subject, and (c) one or more invocable elements for the user to invoke, each of the one or more invocable elements including a single word or a phrase of two or more words representing at least a portion of the determination about the state of the subject, in response to a selection of a particular one of the one or more invocable elements using a first dragging and dropping of the image of the subject onto the particular one of the one or more invocable elements, automatically displaying a tool based on the selected particular invocable element, the tool usable to make a measurement on the image of the subject, the measurement relevant to the attribute of the selected particular invocable element, storing an association between the image of the subject and a numerical result of the measurement, and subsequent to storing the association, in response to a second dragging and dropping by the user of the image of the subject from a second interface onto a first interface that is displayed simultaneously to the second interface in which the image of the subject is displayed, adding the numerical result of the measurement to a structured report expressing the determination about the state of the subject.

* * * * *